US011820814B2

United States Patent
Lauder et al.

(10) Patent No.: US 11,820,814 B2
(45) Date of Patent: Nov. 21, 2023

(54) FACTOR H POTENTIATING ANTIBODIES AND USES THEREOF

(71) Applicants: GEMINI THERAPEUTICS SUB, INC., Cambridge, MA (US); STICHTING SANQUIN BLOEDVOORZIENING, Amsterdam (NL)

(72) Inventors: Scott Lauder, Somerville, MA (US); Tom Purcell, Mountain View, CA (US); Sridhar Govindarajan, Los Altos, CA (US); Taco Willem Kuijpers, Amsterdam (NL); Diana Wouters, Badhoevedorp (NL); Maria Clara Brouwer, Blokker (NL); Richard Benjamin Pouw, Amsterdam (NL); Taede Rispens, Utrecht (NL); Ilse Jongerius, De Bilt (NL); Gillian Dekkers, Utrecht (NL)

(73) Assignees: GEMINI THERAPEUTICS SUB, INC., Cambridge, MA (US); STICHTING SANQUIN BLOEDVOORZIENING, Amsterdam (NL)

( * ) Notice: Subject to any disclaimer, the term of this patent is extended or adjusted under 35 U.S.C. 154(b) by 0 days.

(21) Appl. No.: 17/627,503

(22) PCT Filed: Jul. 17, 2020

(86) PCT No.: PCT/US2020/042627
§ 371 (c)(1),
(2) Date: Jan. 14, 2022

(87) PCT Pub. No.: WO2021/011903
PCT Pub. Date: Jan. 21, 2021

(65) Prior Publication Data
US 2022/0372120 A1   Nov. 24, 2022

Related U.S. Application Data

(60) Provisional application No. 62/875,309, filed on Jul. 17, 2019.

(51) Int. Cl.
*C07K 16/18* (2006.01)
*A61K 47/60* (2017.01)

(52) U.S. Cl.
CPC .............. *C07K 16/18* (2013.01); *A61K 47/60* (2017.08); *C07K 2317/52* (2013.01); *C07K 2317/55* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 5,530,101 A * | 6/1996 | Queen .................. C07K 16/465 |
| | | 424/143.1 |
| 10,112,993 B2 * | 10/2018 | Kuijpers ................. A61P 13/02 |
| 10,865,238 B1 * | 12/2020 | Patz, Jr. .............. C07K 16/2803 |
| 11,377,487 B2 * | 7/2022 | Kuijpers ................ C07K 16/18 |
| 2008/0318841 A1 | 12/2008 | Chtourou et al. |
| 2009/0004183 A1 | 1/2009 | Taylor et al. |
| 2016/0279221 A1 | 9/2016 | Dutta et al. |
| 2016/0297892 A1 | 10/2016 | Heibroch Petersen et al. |
| 2019/0194304 A1 | 6/2019 | Kuijpers et al. |

FOREIGN PATENT DOCUMENTS

| JP | 2013-538232 A | 10/2013 | |
| JP | 2014-088434 A | 5/2014 | |
| WO | 03080672 A1 | 10/2003 | |
| WO | 2006/012621 A2 | 2/2006 | |
| WO | 2007/056227 | 5/2007 | |
| WO | 2007/066017 A2 | 6/2007 | |
| WO | 2008/154251 A2 | 12/2008 | |
| WO | 2010046715 | 4/2010 | |
| WO | 2011/047146 | 4/2011 | |
| WO | 2011/056997 | 5/2011 | |
| WO | 2012/037370 A1 | 3/2012 | |
| WO | 2013/078223 A1 | 5/2013 | |
| WO | 2014/055835 A1 | 4/2014 | |
| WO | 2016/028150 A1 | 2/2016 | |
| WO | WO-2016028150 A1 * | 2/2016 | ............. A61P 13/02 |
| WO | 2016/033225 | 3/2016 | |
| WO | 2019/139481 A1 | 7/2019 | |
| WO | WO-2019139481 A1 * | 7/2019 | ................ A61P 7/00 |

OTHER PUBLICATIONS

Kipriyanov et al., Mol Biotechnol. Jan. 2004;26(1):39-60.*
U.S. Appl. No. 15/504,983, Factor H Potentiating Antibodies and Uses Thereof, filed Feb. 17, 2017, Issued as U.S. Pat. No. 10,112,993.
U.S. Appl. No. 16/961,737, Factor H Potentiating Antibodies and Uses Thereof, filed Jul. 13, 2020, Pending.
PCT/US2020/042627—International Search Report and Written Opinion, dated Oct. 28, 2020, 9 pages.
Pouw et al., "Potentiation of complement regulator factor H protects human endothelial cells from complement attack in aHUS sera," Blood advances, 3, No. 4 (2019): 621-632.
Nozal et al., "Anti-factor H antibody affecting factor H cofactor activity in a patient with dense deposit disease," Clinical Kidney Journal, 5, No. 2 (2012): 133-136.
Morgan et al., "Structural basis for engagement by complement factor H of C3b on a self surface," Nature Structural & Molecular Biology, 18, No. 4, (2011): 463-471 (20 pages).

(Continued)

*Primary Examiner* — Michael Szperka
(74) *Attorney, Agent, or Firm* — Goodwin Procter LLP

(57) ABSTRACT

Provided herein are novel isolated, synthetic or recombinant antibodies and fragments thereof specific for factor H, or nucleic acids or vectors encoding such antibodies and fragments. Further provided herein is the use of such antibodies, fragments, nucleic acids or vectors for inhibiting complement activation and treatment of disorders associated with complement activation.

22 Claims, No Drawings

Specification includes a Sequence Listing.

(56) References Cited

OTHER PUBLICATIONS

Corey et al., "Mechanistic studies of the effects of anti-factor H antibodies on complement-mediated lysis," The Journal of Biological Chemistry, 275, No. 17, (2000): 12917-12925.
Takahashi et al., "Mouse anti-human 87-H3 antibody M30 light chain variable region cDNA." Nov. 1, 2012, pp. 1-2 (NPL reference No. XP002738082).
Lydon, "Anti-LTA mAb light chain variable region, SEQ ID: 60", Jun. 27, 2013 (NPL reference No. XP002738080) (2 pages).
Gearing, "Mouse anti-CD20 heavy chain variable domain, SEQ ID 19", Apr. 18, 2013, pp. 1-2 (NPL reference No. XP002738081).
Csincsi et al., "FHR-1 Binds to C-reactive protein and enhances rather than inhibits complement activation," Journal of Immunology, No. 199 (2017): 292-303 (14 pages).
Simon et al., "Malaria parasites co-opt human factor H to prevent complement-mediated lysis in the mosquito midgut," Cell Host & Microbe, 13, No. 1 (2013): 29-41.
Prodinger et al., "The C-terminus of factor H: monoclonal antibodies inhibit heparin binding and identify epitopes common to factor H and factor H-related proteins," Biochemical Journal, 331 (1998): 41-47.
Cheng et al., "Complement factor H as a marker for detection of bladder cancer," Clinical Chemistry, 51, No. 5 (2005): 856-863.
Ripoche et al., "The complete amino acid sequence of human complement factor H," Biochemical Journal, 249, No. 2 (1988): 593-602.
Schmidt et al., "Translational mini-review series on complement factor H: structural and functional correlations for factor H," Clinical and Experimental Immunology, 151, No. 1 (2008): 14-24.
Wolbink et al., "Application of a monoclonal antibody against a neoepitope on activated C4 in an ELISA for the quantification of complement activation via the classical pathway," Journal of Immunology Methods, 163, No. 1 (1993): 67-76.
Wouters et al., "Studies on the haemolytic activity of circulating C1q-C3/C4 complexes," Molecular Immunology, 45, No. 7 (2008): 1893-99.
Edwards et al., "The remarkable flexibility of the human antibody repertoire; isolation of over one thousand different antibodies to a single protein, BLyS," Journal of Molecular Biology, 334, No. 1 (2003): 103-118.
Zadura et al., "Factor H autoantibodies and deletion of Complement factor H-Related protein-1 in rheumatic diseases in comparison to atypical hemolytic uremic syndrome," Arthritis Research & Therapy, 14, No. 4 (2012) R185 (11 pages).
Lloyd et al., "Modelling the human immune response: performance of a 1011 human antibody repertoire against a broad panel of therapeutically relevant antigens," Protein Engineering, Design & Selection, 22, No. 3 (2009): 159-168.
Sanchez-Corral et al., "Functional analysis in serum from atypical Hemolytic Uremic Syndrome patients reveals impaired protection of host cells associated with mutations in factor H," Molecular Immunology, 41, No. 1 (2004): 81-84.
Pouw et al., "Complement Factor H-Related Protein 3 Serum Levels Are Low Compared to Factor H and Mainly Determined by Gene Copy Number Variation in CFHR3," PLOS One, 11, No. 3 (2016): e0152164 (13 pages).
Rudikoff, S., et al., "Single amino acid substitution altering antigen-binding specificity", Proc. Natl. Acad. Sci., vol. 79 (1982): 1979-1983.
Tamura, M., et al., "Structural correlates of an anticarcinoma antibody: identification of specificity-determining residues (SDRs) and development of a minimally immunogenic antibody variant by retention of SDRs only", J Immunol, vol. 164 (2000), 1432-41.

* cited by examiner

FACTOR H POTENTIATING ANTIBODIES AND USES THEREOF

CROSS-REFERENCE TO RELATED APPLICATIONS

This application is a U.S. national stage application, filed under 35 U.S.C. § 371, of International Application No. PCT/US2020/042627, filed Jul. 17, 2020, which claims the benefit of and priority to U.S. Provisional Patent Application No. 62/875,309, filed Jul. 17, 2019, the disclosures of each of which are incorporated by reference herein in their entireties for all purposes.

SEQUENCE LISTING

The instant application contains a Sequence Listing which has been submitted electronically in ASCII format and is hereby incorporated by reference in its entirety. Said ASCII copy, created on Jan. 13, 2022, is named GEM-013WOUS_SL.txt and is 18,087 bytes in size.

BACKGROUND OF THE DISCLOSURE

The complement system is an important element of innate immunity that contributes to the protection of many organisms such as mammals against invading pathogens. The complement system consists of over 30 different components which are mainly synthesized in the liver. Activation of the complement system occurs by three different pathways, the classical pathway, the lectin pathway and the alternative pathway. The three pathways converge at the formation of a C3 convertase, which are different for each pathway but have similar activity.

In the classical complement pathway, activation of the complement component (C)1 complex, consisting of C1q, C1r and C1s, occurs upon binding to antibody-antigen complexes. The C1 complex cleaves C4 and C2 leading to the formation of a C3 convertase consisting of C4bC2a. The C3 convertase cleaves C3 into the active components C3a and C3b. In the lectin pathway, mannose binding lectin binds to mannose residues on pathogenic surfaces which activates serine proteases MASP-1 and MASP-2 that are able to cleave C4 and C2. As in the classical pathway, this leads to the formation of the C4bC2a C3 convertase. This C3 convertase can bind C3b to form a C5 convertase. Contrary to the classical and lectin pathways, the alternative pathway has a low level of continuous activity due to spontaneous hydrolysis of C3 to C3(H2O) in plasma. This C3b-like C3(H2O) can form a fluid phase C3 convertase by binding factor B (FB) which in turn is activated into Bb by factor D. Similarly, when C3b binds to a surface, it may bind FB to form C3bB. This complex is cleaved by factor D to C3bBb which is the C3 convertase of the alternative pathway that can be stabilized by properdin (factor P) to C3bBbP. This C3 convertase is able to cleave C3 into C3a and C3b. In addition to this process the alternative pathway acts as amplification loop for the classical and lectin activation pathways as C3b generated in these pathways may act as starting point for the alternative pathway. Thereby, the amplification loop results in a reinforcement of the classical and lectin pathway. The C3 convertase formed in one of the three activation pathways can bind C3b to form a C5 convertase. The C5 convertases of all three complement pathways activate C5 into C5a and C5b which initiates the terminal pathway of the complement system. C5b binds C6, C7, C8 and C9 to form the membrane attack complex (MAC) which forms a transmembrane channel and causes cell lysis.

Next to forming a pore in the membrane of pathogens, complement helps clearing pathogens or altered self-cells by opsonization with C3b molecules and production of pro-inflammatory peptides such as C3a and C5a that attract and activate immune cells to the site of infection. Because of the strong pro-inflammatory nature of complement, host cells are well protected by several membrane and soluble complement-regulating proteins.

The alternative pathway contributes for 80-90% to total complement activity. Regulation of this pathway is therefore crucial. C3(H2O) that is formed by spontaneous hydrolysis of C3, and C3b are generally, if not bound by a pathogen, rapidly inactivated by factor H (FH), factor I (FI) and host cell surface molecules thereby inhibiting the formation of the C3 convertases. CD55 (also termed decay accelerating factor or DAF) binds C3b at the host cell surface. FI cleaves C3b to an inactive form but is dependent on co-factors either expressed on cell surfaces (CD46, MCP) or circulating in plasma (FH).

FH is a plasma glycoprotein that is essential for controlling the alternative pathway of complement both in solution and on cell surfaces. FH binds C3b at the same position as FB, thereby preventing the formation of C3 convertases. FH also has decay accelerating activity, i.e. it promotes the dissociation of alternative pathway C3 convertases once they have been formed. Whether FH binds to C3b is determined by the carbohydrates present on the cell surface. Sialic acid, glycosaminoglycans and heparin present on the host cell surface promotes binding of FH to C3b, whereas binding of C3b to molecules expressed on the surface of pathogens results in binding of FB. FH thus exerts its complement inhibitory activity on host cells but not on the surface of pathogenic cells because the cell surface molecules that bind FH are expressed on host cells but generally not on pathogenic cells. FH contains 20 complement control protein (CCP) domains, numbered 1-20 starting at the N-terminus of FH. The CCP domains are also referred to as short consensus repeats (SCR) or sushi domains. CCPs 1-4 are domains involved in regulation and CCPs 19-20 are involved in binding C3b and CCP s 6, 7, 8, 19 and 20 bind to GAGs and sialic acid expressed at the surface of cells. Antibodies that bind CCP19 and/or CCP20 inhibit activity of FH.

Factor H-related proteins (CFHRs) are plasma glycoproteins related in structure and antigenicity to FH. The FHR proteins are also composed of CCP domains and these bear varying degrees of homology to the CCP domains found in FH. For instance, FHR1 comprises domains corresponding to CCP6, CCP7, CCP18, CCP19 and CCP20. In contrast to FH, CFHRs have no strong complement inhibitory activity. A common feature of CFHRs is that they bind to the C3b component of complement, thereby competing with FH for binding to C3b and are thus considered to be positive regulators of the alternative pathway of complement.

FH deficiency or impaired recognition of host surfaces due to mutations is associated with complement-mediated tissue damage and disease. Next to controlling complement activation during normal hemostasis, FH also plays an important role in limiting complement mediated damage of diseased cells and tissues. Multiple mutations in the FH gene have been described that may lead to loss of function of the FH protein. The C-terminal region of FH is a hotspot for mutations in disease. This is a critical region for binding of FH to host cells. Most disease-associated mutations in this region interfere with FH binding. Most patients with a mutated FH gene have heterozygous mutations, meaning that approximately half of the circulating FH has normal function. However, this apparently is not sufficient to protect self surfaces in certain conditions in which complement is activated. FH deficiency may lead to kidney disease such as membranoproliferative glomerulonephritis (MPGN) and atypical hemolytic uremic syndrome (aHUS). More recently a relationship has been described between FH mutations and age-related macular disease (AMD).

Currently the standard treatment for FH deficiency, such as in aHUS, is plasma supplementation or plasma exchange therapy. With such therapy deficient complement regulators are supplemented. Plasma exchange therapy in addition removes mutant complement factors and/or autoantibodies directed against complement factors. However, plasma therapy also has some limitations. No prospective clinical studies have shown that plasma exchange therapy is safe or effective in treating aHUS and efficiency of plasma therapy may depend on the underlying mutations. Some patients develop anaphylactic reactions to fresh frozen plasma, which may require cessation of any form of plasma therapy. Moreover, plasma exchange may worsen the clinical picture of aHUS due to the administration of plasma-derived active pathogenic complement components.

Recently the therapeutic monoclonal antibody eculizumab has been approved for treatment of aHUS and paroxysmal nocturnal hemoglobinuria (PNH) in several countries, among which the US and European countries. Eculizumab is a humanized mouse monoclonal antibody specific for C5 that prevents cleavage of C5 to C5a and C5b. It thus prevents activation of the terminal pathway and decreases the influx of immune cells. However, the use of eculizumab is associated with unwanted side effects. As it blocks C5, which is a crucial component for the initiation of the terminal pathway, patients treated with eculizumab become vulnerable to infection with encapsulated bacteria (such as *Neisseria meningitidis*), the clearance of which is very dependent on MAC formation. Therefore, vaccination against the meningococcus is required for patients prior to receiving treatment with eculizumab. Further, since eculizumab acts downstream of C3, C3 deposition is maintained, which is detrimental in several disorders involving unwanted or excessive complement activation. In addition, high costs are involved with eculizumab treatment and the availability of the antibody is limited.

A mouse monoclonal antibody that binds CCP18 is described by Cheng et al. (Clinical Chemistry, 2005). It is described that this antibody, called X52.1, increases binding of FH to C3b and C3d which is thought to be caused by dimerization of FH. The increased binding of FH to C3b and C3d induced by X52.1 results in an increased complement mediated lysis of cells, including RBCs and several types of cancer cells as shown by Corey et al. (J Biol Chem. 2000). This demonstrates that antibody X52.1 inhibits the complement inhibitory activity of FH. Indeed, Corey et al. suggests that the antibody can be used in the treatment of cancer by enhancing complement-mediated lysis of cancer cells.

There is a continuous need for novel and improved therapeutic agents that bind FH, such as agent that are useful in the treatment of disorders associated with unwanted or excessive complement activation.

SUMMARY OF THE DISCLOSURE

The present invention provides antibodies or antigen binding fragments thereof, for example, isolated, synthetic or recombinant antibodies or antigen binding fragments thereof, that specifically bind complement control protein domain 18 (CCP18) of factor H (FH). Such antibodies and antigen binding fragments are useful for potentiating the activity of FH, for example, increasing the binding affinity of FH to C3b, increasing the ability of FH to inhibit C3 deposition, and/or increasing the ability of FH to inhibit hemolytic activity. In some embodiments, the antibody or fragment comprises: a light chain CDR1 sequence comprising the sequence SSVTY (SEQ ID NO: 1) or the sequence TSVTY (SEQ ID NO: 13); a light chain CDR2 sequence comprising the sequence ATS (SEQ ID NO: 2) or the sequence ASS (SEQ ID NO: 14); a light chain CDR3 sequence comprising the sequence QHRSSSNPLT (SEQ ID NO: 3); a heavy chain CDR1 sequence comprising the sequence GFSLTNYG (SEQ ID NO: 5); a heavy chain CDR2 sequence comprising the sequence VWSGGTT (SEQ ID NO: 6) or the sequence of IWSGGTT (SEQ ID NO: 10); and a heavy chain CDR3 sequence comprising the sequence ARNFGNYAMDY (SEQ ID NO: 7) or the sequence ARNFGNYAMDF (SEQ ID NO: 11).

In some embodiments, the antibody or fragment comprises: a light chain CDR1 sequence comprising the sequence SSVTY (SEQ ID NO: 1); a light chain CDR2 sequence comprising the sequence ATS (SEQ ID NO: 2); a light chain CDR3 sequence comprising the sequence QHRSSSNPLT (SEQ ID NO: 3); a heavy chain CDR1 sequence comprising the sequence GFSLTNYG (SEQ ID NO: 5); a heavy chain CDR2 sequence comprising the sequence IWSGGTT (SEQ ID NO: 10); and a heavy chain CDR3 sequence comprising the sequence ARNFGNYAMDF (SEQ ID NO: 11). In some embodiments, the antibody or fragment comprises: a variable light chain sequence comprising a sequence which has at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 4 or 16, and a variable heavy chain sequence comprising a sequence which has at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 8 or 12. In some embodiments, the antibody or fragment comprises a variable light chain sequence comprising a sequence which has at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 4, and a variable heavy chain sequence comprising a sequence which has at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 12.

In some embodiments, the antibody or fragment comprises: a light chain CDR1 sequence comprising the sequence SSVTY (SEQ ID NO: 1); a light chain CDR2 sequence comprising the sequence ATS (SEQ ID NO: 2); a light chain CDR3 sequence comprising the sequence QHRSSSNPLT (SEQ ID NO: 3); a heavy chain CDR1 sequence comprising the sequence GFSLTNYG (SEQ ID NO: 5); a heavy chain CDR2 sequence comprising the sequence VWSGGTT (SEQ ID NO: 6); and a heavy chain CDR3 sequence comprising the sequence ARNFGNYAMDY (SEQ ID NO: 7). In some embodiments, the antibody or fragment comprises a variable light chain sequence comprising a sequence which has at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 4, and a variable heavy chain sequence comprising a sequence which has at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 8.

In some embodiments, the antibody or fragment comprises: a light chain CDR1 sequence comprising the sequence TSVTY (SEQ ID NO: 13); a light chain CDR2 sequence comprising the sequence ASS (SEQ ID NO: 14); a light chain CDR3 sequence comprising the sequence QHRSSSNPLT (SEQ ID NO: 3); a heavy chain CDR1 sequence comprising the sequence GFSLTNYG (SEQ ID NO: 5); a heavy chain CDR2 sequence comprising the sequence VWSGGTT (SEQ ID NO: 6); and a heavy chain CDR3 sequence having the sequence ARNFGNYAMDY (SEQ ID NO: 7). In some embodiments, the antibody or fragment comprises a variable light chain sequence comprising a sequence which has at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 16, and a variable heavy chain sequence comprising a sequence which has at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 8.

In some embodiments, the antibody or fragment comprises: a light chain CDR1 sequence comprising the sequence TSVTY (SEQ ID NO: 13); a light chain CDR2 sequence comprising the sequence ASS (SEQ ID NO: 14); a light chain CDR3 sequence comprising the sequence QHRSSSNPLT (SEQ ID NO: 3); a heavy chain CDR1 sequence comprising the sequence GFSLTNYG (SEQ ID NO: 5); a heavy chain CDR2 sequence comprising the sequence IWSGGTT (SEQ ID NO: 10); and a heavy chain CDR3 sequence comprising the sequence ARNFGNYAMDF (SEQ ID NO: 11). In some embodiments, the antibody or fragment comprises a variable light chain sequence comprising a sequence which has at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 16, and a variable heavy chain sequence comprising a sequence which has at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 12.

In some embodiments, the antibody or fragment has a binding affinity for FH with a $K_D$ of $2.5 \times 10^{-8}$ M or less and/or a binding affinity for a FH fragment comprised of CCP18-20 with a $K_D$ of $0.1 \times 10^{-9}$ M or less, or wherein the antibody or fragment has a binding affinity for FH with a $K_D$ of $1.25 \times 10^{-8}$ M or less and/or a binding affinity for a FH fragment comprised of CCP18-20 with a $K_D$ of $0.04 \times 10^{-9}$ M or less. In some embodiments, the antibody or fragment has a binding affinity for FH with a $K_D$ of $2.5 \times 10^{-8}$ M or less and/or a binding affinity for a FH fragment comprised of CCP18-20 with a $K_D$ of $0.1 \times 10^{-9}$ M or less, or wherein the antibody or fragment has a binding affinity for FH with a $K_D$ of $0.6 \times 10^{-8}$ M or less and/or a binding affinity for a FH fragment comprised of CCP18-20 with a $K_D$ of $0.6 \times 10^{-11}$ M or less. In some embodiments, the antibody or fragment of the present disclosure: inhibits C3 deposition on lipopolysaccharide (LPS) in vitro in the presence of 10% (v/v) serum with an $IC_{50}$ value of 38 nM or less, such as with an $IC_{50}$ value of 30 nM or less, and/or inhibits hemolytic activity in vitro in the presence of 10% (v/v) serum with an $IC_{50}$ value of 150 nM or less, such as with an $IC_{50}$ value of 130 nM or less, and/or decreases the $K_D$ value (increases binding affinity) of FH for C3b in vitro in the presence of 10% (v/v) serum to 2 µM or less, and/or increases binding affinity of FH for C3b in vitro in the presence of 10% (v/v) serum by at least 3-fold. In certain embodiments, serum is normal human serum.

In some embodiments, the antibody or fragment potentiates FH activity, optionally wherein FH activity is inhibition of alternative complement activation, further optionally wherein inhibition of alternative complement activation comprises: an inhibition of hemolytic activity; an inhibition of complement component 3 (C3) deposition, and/or an increase in binding of FH to C3b, iC3b and/or C3d. In some embodiments, the antibody or fragment comprises an immunoglobulin heavy chain variable region and an immunoglobulin light chain variable region, and wherein the antibody or fragment further comprises an immunoglobulin heavy chain constant region and an immunoglobulin light chain constant region. In some embodiments, the antibody or fragment comprises the constant region of an IgG. In some embodiments, the constant region of the IgG is IgG1, IgG2, IgG3, or IgG4 (e.g., human IgG1, IgG2, IgG3, or IgG4). In some embodiments, the antibody or fragment comprises the constant region of IgG4 (e.g., human IgG4). In some embodiments, the constant region of IgG4 comprises a mutation at position 297. In certain embodiments, the constant region of IgG4 comprises amino acid residue Q at position 297. In certain embodiments, the constant region of IgG4 comprises amino acid residue A at position 297.

In some embodiments, the fragment comprises at least a Fab fragment. In some embodiments, the antibody or fragment is a monoclonal antibody or fragment thereof. In some embodiments, the antibody or fragment is a chimeric or humanized antibody or fragment thereof, comprising human light chain and heavy chain constant regions. In some embodiments, the antibody or fragment is PEGylated. In some embodiments, the antibody or fragment is a PEGylated Fab fragment.

In some embodiments, the disclosure provides for an isolated, synthetic or recombinant nucleic acid comprising a nucleic acid sequence encoding any of the antibodies or fragments disclosed herein. In some embodiments, the disclosure provides for a vector comprising any of the nucleic acids disclosed herein. In some embodiments, the vector is an AAV vector. In some embodiments, the AAV vector is selected from the group consisting of: AAV1, AAV2, AAV3, AAV4, AAV5, AAV6, AAV7, AAV8, AAV9, AAV10, AAV11, and AAV12.

In some embodiments, the disclosure provides for a recombinant cell comprising any of the nucleic acids disclosed herein or any of the vectors disclosed herein.

In some embodiments, the disclosure provides for a pharmaceutical composition comprising any of the antibodies or fragments disclosed herein, any of the nucleic acids disclosed herein, any of the vectors disclosed herein or any of the recombinant cells disclosed herein, and a pharmaceutically acceptable carrier, diluent and/or excipient.

In some embodiments, the disclosure provides for any of the antibodies or fragments disclosed herein, any of the nucleic acids disclosed herein, any of the vectors disclosed herein for use in therapy. In some embodiments, the disclosure provides for any of the antibodies or fragments disclosed herein, any of the nucleic acids disclosed herein, or any of the vectors disclosed herein for use in inhibiting alternative complement activation. In some embodiments, the disclosure provides for any of the antibodies or fragments disclosed herein, any of the nucleic acids disclosed herein, or any of the vectors disclosed herein for use in the treatment, alleviation or prevention of a disorder associated with alternative pathway complement activation. In some embodiments, the disorder is selected from the group consisting of atypical hemolytic uremic syndrome (aHUS), paroxysmal nocturnal hemoglobinuria (PNH), age-related macular degeneration (AMD), membranoproliferative glomerulonephritis (MPGN), and IgA Nephropathy.

In some embodiments, the disclosure provides for a use of any of the antibodies or fragments disclosed herein, any of the nucleic acids disclosed herein, or any of the vectors disclosed herein for the preparation of a medicament for the treatment, alleviation or prevention of a disorder associated with alternative pathway complement activation. In some embodiments, the disorder is selected from the group consisting of atypical hemolytic uremic syndrome (aHUS), paroxysmal nocturnal hemoglobinuria (PNH), age-related macular degeneration (AMD), membranoproliferative glomerulonephritis (MPGN) and IgA Nephropathy.

In some embodiments, the disclosure provides for a method for treating, alleviating, or preventing a disorder associated with alternative pathway complement activation comprising administering to an individual in need thereof a therapeutically effective amount of any of the antibodies or fragments disclosed herein, any of the nucleic acids disclosed herein, any of the vectors disclosed herein, or any of the pharmaceutical compositions disclosed herein. In some embodiments, the disorder is selected from the group consisting of atypical hemolytic uremic syndrome (aHUS), paroxysmal nocturnal hemoglobinuria (PNH), age-related macular degeneration (AMD), membranoproliferative glomerulonephritis (MPGN), and IgA Nephropathy.

In some embodiments, the disclosure provides for a method for inhibiting alternative complement activation comprising administering to a subject any of the antibodies or fragments disclosed herein, any of the nucleic acids disclosed herein, any of the vectors disclosed herein, or any of the pharmaceutical compositions disclosed herein.

In some embodiments, the disclosure provides for a method for producing any of the antibodies or fragments disclosed herein, the method comprising providing a cell with any of the nucleic acids disclosed herein or any of the vectors disclosed herein, and allowing the cell to translate the nucleic acid sequence comprised by the nucleic acid or vector, thereby producing the antibody or fragment. In some embodiments, the method further comprises harvesting, purifying and/or isolating the antibody or fragment.

DETAILED DESCRIPTION OF THE DISCLOSURE

A. General Techniques and Definitions

Unless otherwise defined herein, scientific and technical terms recited herein shall have the meanings that are commonly understood by those of ordinary skill in the art. Generally, nomenclature used in connection with, and techniques of, pharmacology, cell and tissue culture, molecular biology, cell and cancer biology, neurobiology, neurochemistry, virology, immunology, microbiology, genetics and protein and nucleic acid chemistry, described herein, are those well-known and commonly used in the art. In case of conflict, the present specification, including definitions, will control.

The practice of the present disclosure will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Sambrook and Russell, Molecular Cloning: A Laboratory Manual, 3rd. ed., Cold Spring Harbor Laboratory Press, Cold Spring Harbor, NY (2001); Ausubel et al., Current Protocols in Molecular Biology, John Wiley & Sons, NY (2002); Harlow and Lane Using Antibodies: A Laboratory Manual, Cold Spring Harbor Laboratory Press, Cold Spring Harbor, NY (1998); Coligan et al., Short Protocols in Protein Science, John Wiley & Sons, NY (2003); Short Protocols in Molecular Biology (Wiley and Sons, 1999).

Enzymatic reactions and purification techniques are performed according to manufacturer's specifications, as commonly accomplished in the art or as described herein. The nomenclatures used in connection with, and the laboratory procedures and techniques of, analytical chemistry, biochemistry, immunology, molecular biology, synthetic organic chemistry, and medicinal and pharmaceutical chemistry described herein are those well known and commonly used in the art. Standard techniques are used for chemical syntheses, and chemical analyses.

Throughout this specification and embodiments, the word "comprise," or variations such as "comprises" or "comprising," will be understood to imply the inclusion of a stated integer or group of integers but not the exclusion of any other integer or group of integers.

It is understood that wherever embodiments are described herein with the language "comprising," otherwise analogous embodiments described in terms of "consisting of" and/or "consisting essentially of" are also provided.

The term "including" is used to mean "including but not limited to." "Including" and "including but not limited to" are used interchangeably.

Any example(s) following the term "e.g." or "for example" is not meant to be exhaustive or limiting.

Unless otherwise required by context, singular terms shall include pluralities and plural terms shall include the singular.

The articles "a" and "an" are used herein to refer to one or to more than one (i.e., to at least one) of the grammatical object of the article. By way of example, "an element" means one element or more than one element.

"Treating" a condition or patient refers to taking steps to obtain beneficial or desired results, including clinical results. With respect to a disease or condition (e.g., a disease of the eye), treatment refers to the reduction or amelioration of the progression, severity, and/or duration of an infection (e.g., a disease of the eye or symptoms associated therewith), or the amelioration of one or more symptoms resulting from the administration of one or more therapies (including, but not limited to, the administration of one or more prophylactic or therapeutic agents).

As used herein the terms "specific for" and "specifically binds" or "capable of specifically binding" refer to the non-covalent interaction between an antibody and its epitope. It indicates that the antibody or fragment preferentially binds to the epitope over other binding sites or other antigens. Hence, although the antibody or fragment may non-specifically bind to other binding sites or antigens, the binding affinity of the antibody or fragment for its epitope is significantly higher than the binding affinity of the antibody or fragment for any other binding site or antigen.

The percentage of identity of an amino acid sequence or nucleic acid sequence, or the term "% sequence identity", is defined herein as the percentage of residues of the full length of an amino acid sequence or nucleic acid sequence that is identical with the residues in a reference amino acid sequence or nucleic acid sequence after aligning the two sequences and introducing gaps, if necessary, to achieve the maximum percent identity. Methods and computer programs for the alignment are well known in the art, for example "Align 2."

As used herein, "FH.07" refers to an antibody that comprises a variable light chain amino acid sequence of SEQ ID NO: 32 and a variable heavy chain amino acid sequence of SEQ ID NO: 36.

As used herein, "FHR-1.3B4" refers to an antibody that comprises a variable light chain amino acid sequence of SEQ ID NO: 48 and a variable heavy chain amino acid sequence of SEQ ID NO: 52.

In amino acid sequences as depicted herein, amino acids are denoted by single-letter symbols. These single-letter symbols and three-letter symbols are well known to the person skilled in the art and have the following meaning: A (Ala) is alanine, C (Cys) is cysteine, D (Asp) is aspartic acid, E (Glu) is glutamic acid, F (Phe) is phenylalanine, G (Gly) is glycine, H (His) is histidine, I (Ile) is isoleucine, K (Lys) is lysine, L (Leu) is leucine, M (Met) is methionine, N (Asn) is asparagine, P (Pro) is proline, Q (Gln) is glutamine, R (Arg) is arginine, S (Ser) is serine, T (Thr) is threonine, V (Val) is valine, W (Trp) is tryptophan, Y (Tyr) is tyrosine.

With the term "potentiating FH activity" is meant that the activity of FH is increased if an antibody or fragment according to the disclosure binds to FH. In some embodiments, the activity of FH that is potentiated by antibodies and fragments of the disclosure is inhibition of alternative complement activation, such as in an individual. As used herein the term "alternative complement activation" refers to activation of the complement system via the alternative pathway, i.e. involving at least the formation of the C3 convertase of the alternative pathway, i.e. C3bBb/C3bBbP, or involving an increase in the formation of this C3 convertase. Alternative complement activation may further involve cleavage of C3 into C3a and C3b by the alternative pathway C3 convertase, formation of the alternative pathway C5 convertase, i.e. C3bBbC3b/C3bBbC3bP, and/or cleavage of C5 and subsequent binding of C6, C7, C8 and C9 to form the MAC. Alternative complement activation may further include an increase in the alternative pathway amplification loop.

In some embodiments, any of the antibodies or fragments disclosed herein is capable of inhibiting any one or more of the alternative complement activation processes disclosed herein. In some embodiments, the alternative complement activation is inhibited in an individual, (e.g., in a bodily fluid of an individual, such as blood, interstitial fluid or cerebrospinal fluid). As used herein, the term "individual" is used interchangeably with "subject" or "patient" and refers to a human or an animal, such as a mammal (e.g., rodent, simian, equine, bovine, porcine, canine, feline), that comprises a complement system as part of its immune system. In some embodiments, the individual is a mammal. In some embodiments, the mammal is a human.

As used herein "inhibition of alternative complement activation" comprises any alteration in the amount or activity of a component, factor or activity of the alternative complement system that causes or is the result of inhibition thereof. Inhibition of alternative complement activation for instance comprises an inhibition of hemolytic activity, an inhibition of complement component 3 (C3) deposition on cells of the subject, an increase of binding of FH to C3b, iC3b and/or C3d, an inhibition of the formation of the alternative complement pathway C3 convertase C3bBb/C3bBbP, an inhibition of binding of factor B to C3b and/or inhibition of the interaction between C3b and factor B, an inhibition of the cleavage of C3 into C3a and C3b by the alternative pathway C3 convertase, an increase in the binding of FH to host cells, in particular to sialic acid, glycosaminoglycans and/or heparin expressed on host cells, an inhibition of the amplification loop of the alternative complement pathway, and inhibition of the formation of the alternative complement pathway C5 convertase C3bBbC3bP/C3bBbC3bP, an inhibition of the cleavage of C5 to C5a and C5b by the alternative pathway C5 convertase, an increase in the decay accelerating activity of FH, i.e., promotion of the dissociation of alternative pathway C3 convertases once they have formed, and/or an increase in FI co-factor activity resulting in degradation of C3b. In particular embodiments, inhibition of alternative complement activation by FH that is potentiated by the anti-FH antibodies and fragments of the disclosure comprises an inhibition of hemolytic activity, an inhibition of C3 deposition on cells of the subject, and/or an increase of binding of FH to C3b, iC3b and/or C3d.

"Inhibition" as used herein preferably means that the indicated activity is reduced by at least about 25%, at least about 50%, at least about 75%, at least about 80%, at least about 85%, at least about 90%, or at least about 95%. Thus, "inhibition of alternative complement activation" means that the activity of the alternative complement pathway is reduced by at least about 25%, at least about 50%, at least about 75%, at least about 80%, at least about 85%, at least about 90%, or at least about 95%. Similarly, "an inhibition of hemolytic activity" means that hemolytic activity is reduced by at least about 25%, at least about 50%, at least about 75%, at least about 80%, at least about 85%, at least about 90% or, at least about 95%.

"Increase" as used herein preferably means that the indicated activity is increased by at least about 25%, at least about 50%, at least about 75%, at least about 80%, at least about 85%, at least about 90%, or at least about 95%. Thus, "an increase of binding of FH to C3b" means that the binding of FH to C3b is increased by at least about 25%, at least about 50%, at least about 75%, at least about 80%, at least about 85%, at least about 90%, or at least about 95%. Similarly, "an increase in binding of FH to host cells" means that binding of FH to host cells is increased by at least about 25%, at least about 50%, at least about 75%, at least about 80%, at least about 85%, at least about 90%, at least about 95%, at least about 100%, at least about 150%, at least about 200%, at least about 250%, at least about 300%, at least about 350%, at least about 400%, at least about 450%, at least about 500%, at least about 550%, at least about 600%, at least about 700%, at least about 800%, at least about 900%, or at least about 1000%.

As used herein "hemolytic activity" refers to the rupture of red blood cells and the subsequent release of the cell's content into, e.g., the circulation induced by activation of the complement system, preferably as a result of the formation of MAC at the cell surface. Hemolytic activity is for instance measured as described herein in the Examples by using a hemolytic assay as described by Sanchez-Corral et al. (2004) and Wouters et al. (2008), optionally with some modifications. In this representative and non-limiting assay, red blood cells such as sheep red blood cells (SRBCs) are incubated with serum, e.g., human serum, e.g., at 37° C. for 1.25 hours while shaking. Sera with low levels of FH or dysfunctional FH lead to lysis of the SRBCs. Lysis can be stopped by addition of veronal buffer containing 20 mM EDTA followed by centrifugation in a pre-chilled centrifuge (e.g., 7° C.) for 2.5 minutes. The percentage of red blood cell lysis is determined by measuring the absorbance of the supernatants at 412 nm. The serum can for instance be from healthy human individuals or from human individuals suffering from a disorder associated with unwanted or excessive alternative pathway complement activation, such as aHUS. The ability of an antibody or fragment to inhibit hemolytic activity can be determined by incubating the red blood cells with serum in the presence of the antibody or fragment.

"Binding affinity" refers to the strength of the total sum of the noncovalent interactions between a single binding site of an antibody or functional part or functional equivalent and its binding partner (e.g., an antigen). Unless indicated otherwise, as used herein, "binding affinity" refers to intrinsic binding affinity which reflects a 1:1 interaction between members of a binding pair (antibody and antigen in the present application). Binding affinity is herein represented by the equilibrium dissociation constant ($K_D$), which is calculated as the $k_a$ to $k_d$ ratio, see, e.g., Chen, Y., et al., 1999. Affinity can be measured by common methods known in the art, such as for instance a surface plasmon resonance (SPR) assay such as BiaCore (GE Healthcare Life Sciences GE Healthcare Life Sciences) or IBIS-iSPR instrument at IBIS Technologies BV (Hengelo, the Netherlands) or solution phase assays, such as Kinexa.

B. Anti-FH Antibodies and Fragments Thereof

WO 2016/028150 describes a murine agonistic anti-FH antibody, referred to as FH.07, which inhibits alternative pathway activation as shown by an increased binding of FH to C3b, inhibition of mediated C3 deposition and inhibition of hemolytic activity. Fab' and F(ab')2 fragments of the antibody were shown to have the same FH potentiating effect. WO 2019/139481 describes another murine agonistic anti-FH antibody, referred to as FHR-1.3B4, which has greater binding affinity to FH than FH.07 and increased ability to potentiate FH activity.

In one aspect, the present disclosure provides agonistic anti-FH antibodies (e.g., humanized antibodies) and fragments thereof, i.e. antibodies and fragments that potentiate FH activity. In one aspect, these antibodies compete with antibody FH.07 or antibody FHR-1.3B4 for binding to the same epitope in domain CCP18 of FH. Potentiating anti-FH antibodies are potent inhibitors of activation of the alternative complement pathway and therefor useful in the treatment of disorders associated with unwanted or excessive activation of the alternative pathway of the complement system. FH specifically inhibits the amplification loop of the alternative pathway wherein the cleavage of C3 into C3b and subsequent binding thereof to FB at the cell surface and formation of the C3 convertase promotes cleavage of further C3 molecules into C3b. The main advantage of the fact that the antibodies and fragments of the disclosure interfere with complement activation at the level of C3 is that accumulation of C3b on the surface and release of C3a is avoided. Contrary, if complement activation is inhibited at the C5 level, such as with eculizumab, accumulation of C3b and release of C3a is not inhibited. C3b acts as an opsonin and C3a is an anaphylatoxin. Accumulation of C3b and C3a formation is thus preferably prevented, because these processes result in the attraction of immune cells and opsonophagocytosis of the target. This means that for instance PNH patients receiving eculizumab still need transfusions because accumulation of C3b results in opsonization of red blood cells, which are subsequently removed in the liver and spleen. Further, treatment with anti-05 antibodies results in accumulation of C3b and C3a formation on cells that would otherwise be lysed by the MAC. An important disadvantage of anti-05 antibodies is that patients become vulnerable for infections because the antibodies interfere with complement activation induced by pathogens as well. By targeting a regulator of the complement system that protects host cells, this is avoided.

The term "antibody" as used herein, refers to an immunoglobulin protein comprising at least a heavy chain variable region (VH), paired with a light chain variable region (VL), that is specific for a target epitope. The term covers both polyclonal and monoclonal antibodies. It refers to any form of antibody that specifically binds to CCP18 of FH, including full length immunoglobulins. An antibody or fragment thereof according to the disclosure comprises at least one antigen binding site. The term "antigen binding site" as used herein refers to a site of an antibody or fragment thereof comprising at least one CDR sequence, preferably at least two CDR sequences, more preferably at least three CDR sequences. For instance, an antigen binding site comprises light chain CDRs 1-3 or heavy chain CDRs 1-3. In some embodiments, the antigen binding site comprises light chain CDRs 1-3 and heavy chain CDRs 1-3.

As is well known by the skilled person, antibodies contain two heavy chains and two light chains. A heavy chain of an antibody is the larger of the two types of chains making up an immunoglobulin molecule. A heavy chain comprises a constant domain and a variable domain, which variable domain is involved in antigen binding. A light chain of an antibody is the smaller of the two types of chains making up an immunoglobulin molecule. A light chain comprises a constant domain and a variable domain. The variable domain of the light chain is often, but not always, together with the variable domain of the heavy chain involved in antigen binding. Complementary-determining regions (CDRs) are the hypervariable regions present in heavy chain variable domains and light chain variable domains. In case of full length antibodies, the CDRs 1-3 of a heavy chain and the CDRs 1-3 of the connected light chain together form the antigen-binding site.

CDRs are involved in antigen binding and confer antigen specificity and binding affinity to the antibody. There are three CDRs in each of the variable domains of the heavy chain and the light chain, which are designated CDR1, CDR2 and CDR3, for each of the variable domains. The term "CDR set" as used herein refers to a group of three CDRs that occur in a single heavy or light chain variable domain capable of binding a target antigen. The exact boundaries of these CDRs have been defined differently according to different systems. The three heavy chain CDRs can be referred to as CDRH1, CDRH2, and CDRH3, and the three light chain CDRs can be referred to as CDRL1, CDRL2, and CDRL3.

An "antigen binding fragment of an antibody" is defined herein as a part of an antibody that is capable of specifically binding the same antigen as the antibody, e.g., CCP18 of FH, although not necessarily to the same extent. A fragment of an FH activity potentiating antibody further also potentiates FH activity, although not necessarily to the same extent. A fragment of an FH activity inhibiting antibody further also inhibits FH activity, although not necessarily to the same extent. In some embodiments, an antibody fragment according to the disclosure comprises the heavy chain CDR1, CDR2 and CDR3 sequences of an antibody (e.g., any of the antibodies disclosed herein), and in some embodiments further comprises the light chain CDR1, CDR2 and CDR3 sequence of the antibody. Non-limiting examples of a fragment of an antibody are a single domain antibody, a single chain antibody, a nanobody, an unibody, a single chain variable fragment (scFv), a Fab fragment, a Fab' fragment, a F(ab')2 fragment and a F(ab)$_2$ fragment. In some embodiments, a fragment of an antibody comprises at least a heavy chain variable domain (VH) and/or a light chain variable domain (VL). In some embodiments, a fragment comprises at least a Fab fragment. Fab' fragments of potentiating anti-FH antibody FH.07 or antibody FHR-1.3B4, which in some embodiments competes with the antibodies of the present disclosure for binding to the same epitope, has been demonstrated to retain the ability to potentiate the function of FH. In some embodiments, fragments of an antibody of the disclosure are therefore a Fab fragment, a Fab' fragment, a F(ab')2 fragment or a F(ab)$_2$ fragment of antibodies according to the disclosure. In another embodiment, a fragment of an antibody according to the disclosure comprises an immunoglobulin heavy chain variable region, an immunoglobulin heavy chain constant region, an immunoglobulin light chain variable region and an immunoglobulin light chain constant region.

In some embodiments, antibodies and fragments according to the disclosure are able to potentiate the activity of FH, such as of human FH.

In some embodiments, inhibition of C3 deposition is measured using a C3 deposition assay, such as the C3 deposition assay described herein in the Examples. This representative and non-limiting assay involves the coating of microtiterplates with LPS. The plates are subsequently incubated with serum, e.g., from healthy individuals or from individuals suffering from a disorder associated with unwanted or excessive alternative complement activation as indicated above, in the presence or absence of antibody or fragments. C3 deposition on LPS can be detected with an anti-C3 antibody.

In some embodiments, an increase of binding of FH to C3b is measured using an ELISA as described herein in the Examples. This representative and non-limiting assay involves coating of microtiter ELISA plate with C3b and incubation of the plate with serum, e.g., from healthy individuals or from individuals suffering from a disorder associated with unwanted or excessive alternative complement activation as indicated above. Bound FH can be detected with an anti-FH antibody, such as peroxidase-labeled polyclonal anti-FH. The ability of an antibody or fragment to enhance FH binding to C3b can be determined by preincubating the serum in the presence of the antibody or fragment before incubation with the coated C3b. As another example, binding of FH to C3b can be determined using Surface Plasmon Resonance (SPR), for instance, as described herein in the Examples. SPR is a technique to measure biomolecular interactions in real-time in a label free environment. One of the interactants, for instance C3b, is immobilized to a sensor surface, and the other, for instance FH, is free in solution and passed over the surface, e.g., in the presence or absence of (different concentrations of) an antibody or fragment of the disclosure. In some embodiments, antibodies or fragments thereof according to the present disclosure increase binding affinity (decreased $K_D$ value) of FH for C3b in vitro to at most 2 µM, at most 1.95 µM, at most 1.8 µM, at most 1.7 µM and/or increases binding affinity of FH for C3b in vitro at least 2 times, at least 2.5 times, at least 3 times, at least 3.5 times, at least 4 times, at least 4.5 times, at least 5 times, at least 5.5 times, at least 6 times, at least 7 times, at least 8 times, at least 9 times or at least 10 times. In particular embodiments, antibodies or fragments thereof according to the present disclosure increase binding affinity ($K_D$) of FH for C3b in vitro to less than 1 µM, less than 750 nM, less than 500 nM, less than 300 nM or less than 250 nM. In particular embodiments, antibodies or fragments thereof according to the present disclosure increase binding affinity ($K_D$) of FH for C3b in vitro to between 250 nM and 1 µM. In particular embodiments, antibodies or fragments thereof according to the present disclosure increase binding affinity of FH for C3b in vitro at least 3-5 times.

In some embodiments, antibodies or fragments thereof provided by the present disclosure have a low in vitro $IC_{50}$ value in one or more functional assays, such as in some embodiments, an in vitro $IC_{50}$ value that is lower than the in vitro $IC_{50}$ value of antibody FH.07 or antibody FHR-1.3B4 for the same functional assay. "$IC_{50}$" is a term well known in the art and refers to the concentration of an antibody or fragment that is necessary to inhibit or reduce a certain functional activity by 50%. The lower the $IC_{50}$ value of an antibody or fragment, the stronger the inhibiting activity of the antibody or fragment, and the greater its potential as a therapeutic agent. In some embodiments, the functional assay is a C3b deposition assay and/or a hemolytic assay as described herein above. In some embodiments, an antibody or fragment thereof according to the disclosure inhibits C3 deposition on LPS in vitro in the presence of 10% (v/v) normal human serum with an $IC_{50}$ value of 38 nM or less, 35 nM or less, 32 nM or less, 30 nM or less, 28 nM or less, 27 nM or less, 25 nM or less, 23 nM or less, 20 nM or less, 18 nM or less, 15 nM or less, or 10 nM or less. In some embodiments, an antibody or fragment thereof according to the disclosure inhibits C3 deposition on LPS in vitro in the presence of 10% (v/v) normal human serum with an $IC_{50}$ value of between 15 nM and 30 nM. In some embodiments, an antibody or fragment thereof according to the disclosure inhibits hemolytic activity in vitro in the presence of 10% (v/v) normal human serum with an $IC_{50}$ value of 150 nM or less, 130 nM or less, 120 nM or less, 115 nM or less, 110 nM or less, 105 nM or less, 100 nM or less, 95 nM or less, 90 nM or less, 85 nM or less, 80 nM or less, 75 nM or less, 70 nM or less, 65 nM or less, or 60 nM or less. In some embodiments, an antibody or fragment thereof according to the disclosure inhibits hemolytic activity in vitro in the presence of 10% (v/v) normal human serum with an $IC_{50}$ value between 60 nM and 80 nM.

In some embodiments, antibodies or fragment of the disclosure inhibit C3 deposition on LPS in vitro in the presence of 10% (v/v) normal human serum with a low $IC_{50}$ value as described herein above and inhibit hemolytic activity in vitro in the presence of 10% (v/v) normal human serum with a low $IC_{50}$ value as described herein above. In some embodiments, an antibody or fragment according to the disclosure inhibits C3 deposition on LPS in vitro in the presence of 10% (v/v) normal human serum with an $IC_{50}$ value of 38 nM or less and inhibits hemolytic activity in vitro in the presence of 10% (v/v) normal human serum with an $IC_{50}$ value of 150 nM or less, inhibits C3 deposition on LPS in vitro in the presence of 10% (v/v) normal human serum with an $IC_{50}$ value of 30 nM or less and inhibits hemolytic activity in vitro in the presence of 10% (v/v) normal human serum with an $IC_{50}$ value of 150 nM or less, or inhibits C3 deposition on LPS in vitro in the presence of 10% (v/v) normal human serum with an $IC_{50}$ value of 27 nM or less and inhibits hemolytic activity in vitro in the presence of 10% (v/v) normal human serum with an $IC_{50}$ value of 100 nM or less. In some embodiments, the $IC_{50}$ value for C3 deposition on LPS in vitro in the presence of 10% (v/v) normal human serum is determined in a C3 deposition assay as described herein above. In some embodiments, the $IC_{50}$ value for hemolytic activity is determined in a hemolytic activity assay as described herein above.

In some embodiments, antibodies or fragments thereof provided by the present disclosure have a high binding affinity for FH and/or a FH fragment comprising domains CCP18-20, such as n some embodiments a binding affinity that is higher than the binding affinity of antibody FH.07 or antibody FHR-1.3B4. In some embodiments, in vivo therapeutic activity of an antibody or fragment typically requires high binding affinity, e.g., to minimize binding of the antibody or fragment to binding sites and/or antigens other than the epitope or antigen it is specific for and to minimize the amount of antibody or fragment that needs to be administered in vivo. In some embodiments, antibodies with a high binding affinity are preferred. In some embodiments, an antibody or fragment thereof has a binding affinity for FH with a dissociation constant ($K_D$) of $2.5 \times 10^{-8}$ M or less and/or a binding affinity for a FH fragment comprised of CCP18-20 with a $K_D$ of $0.1 \times 10^{-9}$ M or less. In one embodiment, the disclosure therefore provides an isolated, synthetic or recombinant antibody or antigen binding fragment thereof that specifically binds to factor H (FH) and potentiates FH activity, wherein the antibody has a binding affinity for FH with a $K_D$ of $2.5 \times 10^{-8}$ M or less and/or a binding affinity for a FH fragment comprised of CCP18-20 with a $K_D$ of $0.1 \times 10^{-9}$ M or less. In some embodiments, an antibody or fragment according to the disclosure has a binding affinity for FH with a $K_D$ of 22.5 nM or less, 20 nM or less, 17.5 nM or less, 15 nM or less, 12.5 nM or less, 10 nM or less, 9 nM or less, 8 nM or less, 7 nM or less, 6 nM or less, 5 nM or less, 4 nM or less, 3 nM or less, 2 nM or less, 1 nM or less, 0.9 nM or less, 0.8 nM or less, 0.7 nM or less, or 0.6 nM or less. In some embodiments, an antibody or fragment according to the disclosure has a binding affinity for a FH fragment comprised of CCP18-20 with a $K_D$ of $0.09 \times 10^{-9}$ M or less, $0.08 \times 10^{-9}$ M or less, $0.07 \times 10^{-9}$ M or less, $0.06 \times 10^{-9}$ M or less, $0.05 \times 10^{-9}$ M or less, $0.04 \times 10^{-9}$ M or less, $0.03 \times 10^{-9}$ M or less, $0.02 \times 10^{-9}$ M or less, $1 \times 10^{-11}$ M or less, $0.9 \times 10^{-11}$ M or less, $0.8 \times 10^{-11}$ M or less, $0.7 \times 10^{-11}$ M or less, or $0.6 \times 10^{-11}$ M or less. In some embodiments, an antibody or fragment thereof has a binding affinity for FH with a $K_D$ of $1.25 \times 10^{-8}$ M or less and/or a binding affinity for a FH fragment comprised of CCP18-20 with a $K_D$ of $0.04 \times 10^{-9}$ M or less. In some embodiments, an antibody or fragment thereof has a binding affinity for FH with a $K_D$ of $0.6 \times 10^{-8}$ M or less and/or a binding affinity for a FH fragment comprised of CCP18-20 with a $K_D$ of $0.6 \times 10^{-11}$ M or less. In some embodiments, the binding affinity is determined using surface plasmon resonance (SPR), such as using SPR in an assay as described herein, i.e., in an assay wherein binding affinity is determined by SPR on a ProtA chip, capturing the antibody or fragment before flowing either full length FH (for binding affinity for FH) or a fragment of FH comprised of domain 18-20 (for binding affinity for CCP18-20) over the surface.

In some embodiments, antibodies or fragments thereof provided by the present disclosure increases interaction of FH with C3b. In some embodiments, an antibody or fragment thereof increases the binding affinity of FH for C3b with a dissociation constant ($K_D$) of 2 µM or less. In some embodiments, an antibody or fragment according to the disclosure increases binding affinity for C3b with a $K_D$ of 2 µM or less, 1.5 µM or less, 1 µM or less, 500 nM or less, 400 nM or less, or 300 nM or less. In some embodiments, an antibody or fragment according to the disclosure increases binding affinity of FH for C3b in vitro (reduces the $K_D$) by at least 2.5-fold, 3-fold, 3.5-fold, 4-fold, 4.5-fold, or 5-fold.

In some embodiments, antibodies or fragments according to the disclosure have a high binding affinity and inhibit C3 deposition on LPS in vitro with a low $IC_{50}$ value and/or inhibit hemolytic activity in vitro with a low $IC_{50}$ value. In some embodiments, an antibody or fragment according to the disclosure has a binding affinity for FH with a $K_D$ of $2.5 \times 10^{-8}$ M or less and/or a binding affinity for a FH fragment comprised of CCP18-20 with a $K_D$ of $0.1 \times 10^{-9}$ M or less and inhibits C3 deposition on LPS in vitro in the presence of 10% (v/v) normal human serum with an $IC_{50}$ value of 38 nM or less and/or inhibits hemolytic activity in vitro in the presence of 10% (v/v) normal human serum with an $IC_{50}$ value of 150 nM or less. In some embodiments, the antibody or fragment has a binding affinity for FH with a $K_D$ of $1.25 \times 10^{-8}$ M or less (e.g., 10 nM or less, 5 nM or less, or 1 nM or less) and/or a binding affinity for a FH fragment comprised of CCP18-20 with a $K_D$ of $0.04 \times 10^{-9}$ M or less and inhibits C3 deposition on LPS in vitro with an $IC_{50}$ value of 30 nM or less and inhibits hemolytic activity in vitro in the presence of 10% (v/v) normal human serum with an $IC_{50}$ value of 115 nM or less. In some embodiments, the antibody or fragment has a binding affinity for FH with a $K_D$ of $1.25 \times 10^{-8}$ M or less (e.g., 10 nM or less, 5 nM or less, or 1 nM or less) and/or a binding affinity for a FH fragment comprised of CCP18-20 with a $K_D$ of $0.04 \times 10^{-9}$ M or less and inhibits C3 deposition on LPS in vitro in the presence of 10% (v/v) normal human serum with an $IC_{50}$ value of 27 nM or less and inhibits hemolytic activity in vitro in the presence of 10% (v/v) normal human serum with an $IC_{50}$ value of 100 nM or less. In some embodiments, the antibody or fragment has a binding affinity for FH with a $K_D$ of $1.25 \times 10^{-8}$ M or less (e.g., 10 nM or less, 5 nM or less, or 1 nM or less) and/or a binding affinity for a FH fragment comprised of CCP18-20 with a $K_D$ of $0.04 \times 10^{-9}$ M or less and inhibits C3 deposition on LPS in vitro in the presence of 10% (v/v) normal human serum with an $IC_{50}$ value of 25 nM or less and inhibits hemolytic activity in vitro in the presence of 10% (v/v) normal human serum with an $IC_{50}$ value of 80 nM or less. In some embodiments, the antibody or fragment has a binding affinity for FH with a $K_D$ of $1.25 \times 10^{-8}$ M or less (e.g., 10 nM or less, 5 nM or less, or 1 nM or less) and/or a binding affinity for a FH fragment comprised of CCP18-20 with a $K_D$ of $0.04 \times 10^{-9}$ M or less and inhibits C3 deposition on LPS in vitro in the presence of 10% (v/v) normal human serum with an $IC_{50}$ value of between 15 nM and 25 nM and inhibits hemolytic activity in vitro in the presence of 10% (v/v) normal human serum with an $IC_{50}$ value of between 15 nM and 25 nM. In some embodiments, the binding affinity is determined by SPR as described herein. In some embodiments, the $IC_{50}$ value for C3 deposition on LPS in vitro is determined in a C3 deposition assay as described herein above. In some embodiments, the $IC_{50}$ value for hemolytic activity is determined in a hemolytic activity assay as described herein above.

In some embodiments, any of the antibodies or antigen binding fragments disclosed herein have a higher binding affinity for FH and/or a FH fragment comprising CCP18 than the binding affinity of antibody FH.07. In some embodiments, any of the antibodies or antigen binding fragments disclosed herein have a higher binding affinity for FH and/or a FH fragment comprising CCP18-20 than the binding affinity of antibody FH.07. In some embodiments, any of the antibodies or antigen binding fragments disclosed herein have a $IC_{50}$ value that is lower than the $IC_{50}$ value of antibody FH.07. In some embodiments, any of the antibodies or antigen binding fragments disclosed herein shows greater inhibition of C3 deposition on LPS than antibody FH.07. In some embodiments, any of the antibodies or antigen binding fragments disclosed herein shows greater inhibition of hemolytic activity than antibody FH.07. In some embodiments, any of the antibodies or antigen binding fragments disclosed herein competes for binding to the same epitope in CCP18 of FH with antibody FH.07. In some embodiments, any of the antibodies or antigen binding fragments disclosed herein have high storage ability, in particular an improved storage stability as compared to antibody FH.07. In some embodiments, any of the antibodies or antigen binding fragments disclosed herein have high stability, in particular an improved stability as compared to antibody FH.07. In some embodiments, any of the antibodies or antigen binding fragments disclosed herein have a high selectivity, in particular an increased selectivity as compared to antibody FH.07.

In some embodiments, any of the antibodies or antigen binding fragments disclosed herein have a higher binding affinity for FH and/or a FH fragment comprising CCP18 than the binding affinity of antibody FHR-1.3B4. In some embodiments, any of the antibodies or antigen binding fragments disclosed herein have a higher binding affinity for FH and/or a FH fragment comprising CCP18-20 than the binding affinity of antibody FHR-1.3B4. In some embodiments, any of the antibodies or antigen binding fragments disclosed herein have a $IC_{50}$ value that is lower than the $IC_{50}$ value of antibody FHR-1.3B4. In some embodiments, any of the antibodies or antigen binding fragments disclosed herein inhibits C3 deposition on LPS better than antibody FHR-1.3B4. In some embodiments, any of the antibodies or antigen binding fragments disclosed herein shows greater inhibition of hemolytic activity than antibody FHR-1.3B4. In some embodiments, any of the antibodies or antigen binding fragments disclosed herein competes for binding to the same epitope in CCP18 of FH as antibody FHR-1.3B4. In some embodiments, any of the antibodies or antigen binding fragments disclosed herein have high storage ability, in particular an improved storage stability as compared to antibody FHR-1.3B4. In some embodiments, any of the antibodies or antigen binding fragments disclosed herein have high stability, in particular an improved stability as compared to antibody FHR-1.3B4. In some embodiments, any of the antibodies or antigen binding fragments disclosed herein have a high selectivity, in particular an increased selectivity as compared to antibody FHR-1.3B4.

In some embodiments, the antibodies or fragments thereof provided by the present disclosure competes with antibody anti FH.07 for binding to FH, in particular to CCP18 domain of FH.

Table 1 lists exemplary antibodies of the present disclosure. The CDR sequences are numbered according to the IMGT numbering system (Lefranc 1997, Lefranc 1999 and Lefranc et al. 2003). LC=light chain, HC=heavy chain, CDR=Complementary-determining regions, VH=heavy chain variable region, VL=light chain variable region.

TABLE 1

Amino acid and nucleotide sequences of Antibodies 1-4, FH.07, and FHR-1.3B4

| Antibody | Type | Identity | Sequence | SEQ ID NO |
|---|---|---|---|---|
| Antibody 1 | amino acid | LC CDR1 | SSVTY | 1 |
| Antibody 1 | amino acid | LC CDR2 | ATS | 2 |
| Antibody 1 | amino acid | LC CDR3 | QHRSSSNPLT | 3 |
| Antibody 1 | amino acid | VL | DIQLTQSPSSLSASVGDRVTITCK ASSSVTYLHWYQQKPGKAPKPLI YATSNLASGVPSRFSGSGSGTDFT LTISSLQPEDFATYYCQHRSSSNP LTFGAGTKLELK | 4 |
| Antibody 1 | amino acid | HC CDR1 | GFSLTNYG | 5 |
| Antibody 1 | amino acid | HC CDR2 | VWSGGTT | 6 |
| Antibody 1 | amino acid | HC CDR3 | ARNFGNYAMDY | 7 |
| Antibody 1 | amino acid | VH | QVQLQESGPGLVKPSQTLSLTCT VSGFSLTNYGVYWIRQHPGKGLE WIGVVWSGGTTEFNPSLKSRVTI SKDTSKNQVSLKLSSVTAADTAV YYCARNFGNYAMDYWGQGTSV TVSS | 8 |
| Antibody 2 | amino acid | LC CDR1 | SSVTY | 1 |
| Antibody 2 | amino acid | LC CDR2 | ATS | 2 |

TABLE 1-continued

Amino acid and nucleotide sequences of Antibodies 1-4, FH.07, and FHR-1.3B4

| Antibody | Type | Identity | Sequence | SEQ ID NO |
|---|---|---|---|---|
| Antibody 2 | amino acid | LC CDR3 | QHRSSSNPLT | 3 |
| Antibody 2 | amino acid | VL | DIQLTQSPSSLSASVGDRVTITCK ASSSVTYLHWYQQKPGKAPKPLI YATSNLASGVPSRFSGSGSGTDFT LTISSLQPEDFATYYCQHRSSSNP LTFGAGTKLELK | 4 |
| Antibody 2 | amino acid | HC CDR1 | GFSLTNYG | 5 |
| Antibody 2 | amino acid | HC CDR2 | IWSGGTT | 10 |
| Antibody 2 | amino acid | HC CDR3 | ARNFGNYAMDF | 11 |
| Antibody 2 | amino acid | VH | QVQLQESGPGLVKPSQTLSLTCT VSGFSLTNYGVYWIRQHPGKGLE WIGVIWSGGTTEYNPSMKSRVTI SKDTSKNQVSLKLSSVTAADTAV YYCARNFGNYAMDFWGQGTSV TVSS | 12 |
| Antibody 3 | amino acid | LC CDR1 | TSVTY | 13 |
| Antibody 3 | amino acid | LC CDR2 | ASS | 14 |
| Antibody 3 | amino acid | LC CDR3 | QHRSSSNPLT | 3 |
| Antibody 3 | amino acid | VL | DIQLTQSPSSLSASVGDRVTITCR ASTSVTYMHWYQQKPGKAPKPL IYASSNLASGVPSRFSGSGSGTDF TLTISSLQPEDFATYYCQHRSSSN PLTFGAGTKLELK | 16 |
| Antibody 3 | amino acid | HC CDR1 | GFSLTNYG | 5 |
| Antibody 3 | amino acid | HC CDR2 | VWSGGTT | 6 |
| Antibody 3 | amino acid | HC CDR3 | ARNFGNYAMDY | 7 |
| Antibody 3 | amino acid | VH | QVQLQESGPGLVKPSQTLSLTCT VSGFSLTNYGVYWIRQHPGKGLE WIGVVWSGGTTEFNPSLKSRVTI SKDTSKNQVSLKLSSVTAADTAV YYCARNFGNYAMDYWGQGTSV TVSS | 8 |
| Antibody 4 | amino acid | LC CDR1 | TSVTY | 13 |
| Antibody 4 | amino acid | LC CDR2 | ASS | 14 |
| Antibody 4 | amino acid | LC CDR3 | QHRSSSNPLT | 3 |
| Antibody 4 | amino acid | VL | DIQLTQSPSSLSASVGDRVTITCR ASTSVTYMHWYQQKPGKAPKPL IYASSNLASGVPSRFSGSGSGTDF TLTISSLQPEDFATYYCQHRSSSN PLTFGAGTKLELK | 16 |
| Antibody 4 | amino acid | HC CDR1 | GFSLTNYG | 5 |
| Antibody 4 | amino acid | HC CDR2 | IWSGGTT | 10 |
| Antibody 4 | amino acid | HC CDR3 | ARNFGNYAMDF | 11 |
| Antibody 4 | amino acid | VH | QVQLQESGPGLVKPSQTLSLTCT VSGFSLTNYGVYWIRQHPGKGLE WIGVIWSGGTTEYNPSMKSRVTI SKDTSKNQVSLKLSSVTAADTAV YYCARNFGNYAMDFWGQGTSV TVSS | 12 |
| FH.07 | amino acid | LC CDR1 | SSVKY | 29 |
| FH.07 | amino acid | LC CDR2 | ATS | 30 |

TABLE 1-continued

Amino acid and nucleotide sequences of Antibodies 1-4, FH.07, and FHR-1.3B4

| Antibody | Type | Identity | Sequence | SEQ ID NO |
|---|---|---|---|---|
| FH.07 | amino acid | LC CDR3 | QQWSIIPPT | 31 |
| FH.07 | amino acid | VL | QIVLSQSPTFLSASPGEKVTVTCR ASSSVKYMHWYQQKPGASPKPW IFATSNLASGVPARFSGSGSGTSY SLTISRVEAEDAATYYCQQWSIIP PTFGNGTKLELK | 32 |
| FH.07 | amino acid | HC CDR1 | DFSLARYG | 33 |
| FH.07 | amino acid | HC CDR2 | IWSGGTA | 34 |
| FH.07 | amino acid | HC CDR3 | ARNFGNYAVDY | 35 |
| FH.07 | amino acid | VH | QVQLQQSGPGLVQPSQSLSITCTV SDFSLARYGVHWIRQSPGKGLE WLGVIWSGGTADYNAAFISRLNI NKDNSKSQVFFKMNSLQANDTAI YYCARNFGNYAVDYWGQGTS | 36 |
| FH.07 | nucleic acid | LC CDR1 | tcaagtgtcaaatac | 17 |
| FH.07 | nucleic acid | LC CDR2 | gccacatcc | 18 |
| FH.07 | nucleic acid | LC CDR3 | cagcagtggagtattatcccacccacg | 19 |
| FH.07 | nucleic acid | VL | caaattgttctctcccagtctccaacattcctgtctgca tctccaggtgagaaggtcacagtgacttgcagggc cagttcaagtgtcaaatacatgcactggtatcagcag aaaccaggagcctcccccaaaccctggattttttgcc acatccaacctggcttctggagtccctgctcgcttca gtggcagtgggtctgggacctcttattctctcacaat cagcagagtggaggctgaagatgctgccacttatta ctgccagcagtggagtattatcccacccacgttcgg taatgggaccaagctggagctgaaac | 20 |
| FH.07 | nucleic acid | HC CDR1 | gatttctcattagctaggtatggt | 21 |
| FH.07 | nucleic acid | HC CDR2 | atatggagtggtggaaccgca | 22 |
| FH.07 | nucleic acid | HC CDR3 | gccagaaattttggtaactacgctgtggactac | 23 |
| FH.07 | nucleic acid | VH | caggtgcagctgcagcagtcaggacctggcctagt gcagccctctcagagcctgtccattacctgcacagt ctctgatttctcattagctaggtatggtgtacactggat tcgccagtctccaggaaagggtctggagtggctgg gagtgatatggagtggtggaaccgcagactataatg cagctttcatatccagactgaacatcaacaaggaca attccaagagccaagttttctttaaaatgaacagtctc caagctaatgacacagccatatattactgtgccaga aattttggtaactacgctgtggactactggggtcaag gaacctcag | 24 |
| FHR-1.3B4 | amino acid | LC CDR1 | SSVTY | 45 |
| FHR-1.3B4 | amino acid | LC CDR2 | ATS | 46 |
| FHR-1.3B4 | amino acid | LC CDR3 | QQRSSSNPLT | 47 |
| FHR-1.3B4 | amino acid | VL | QIVLSQSPTILSASPGEKVTMTCR ASSSVTYMHWYQQKPGSSPKPW IYATSNLASGVPARFSGSGSGTSY SLTISRVEAEDAATYYCQQRSSS NPLTFGAGTKLELK | 48 |
| FHR-1.3B4 | amino acid | HC CDR1 | GFSLTNYG | 49 |

TABLE 1-continued

Amino acid and nucleotide sequences of Antibodies 1-4, FH.07, and FHR-1.3B4

| Antibody | Type | Identity | Sequence | SEQ ID NO |
|---|---|---|---|---|
| FHR-1.3B4 | amino acid | HC CDR2 | IWSGGTT | 50 |
| FHR-1.3B4 | amino acid | HC CDR3 | ARNFGNYAMDY | 51 |
| FHR-1.3B4 | amino acid | VH | QVQLRQSGPGLVQPSQSLSITCTV SGFSLTNYGVYWVRQSPGKGLE WLGVIWSGGTTDYSAAFISRLSIS KDNSKSQVFFKMNSLQADDTAIY YCARNFGNYAMDYWGQGTSVT VSS | 52 |
| FHR-1.3B4 | nucleic acid | VL | caaattgttctctcccagtctccaacaatcctgtctgc atctccaggggagaaggtcacaatgacttgcaggg ccagctcaagtgtaacttacatgcactggtaccagc agaagccaggatcctcccccaaaccctggatttatg ccacatccaacctggcttctggagtccctgctcgctt cagtggcagtgggtctgggacctcttactctctcaca atcagcagagtggaggctgaagatgctgccacttat tactgccagcagcgcagtagtagtaacccgctcac gttcggtgctgggaccaagctggagctgaaat | 25 |
| FHR-1.3B4 | nucleic acid | VH | caggtgcagctgaggcagtcaggacctggcctagt gcagccctcacagagcctgtccatcacctgcacagt ctctggtttctcattaactaactatggtgtatattgggtt cgccagtctccaggaaagggtctggagtggctggg agtgatatggagtggaggaaccactgactatagtgc agctttcatatccagactgagcatcagcaaggacaa ctccaagagccaagttttctttaaaatgaacagtctgc aagctgatgacacagccatatactactgtgccagaa tttggcactacgctatggactacatggggtcaagga acctcacaccggtctccacag | 26 |

In some embodiments, the disclosure provides for an isolated, synthetic or recombinant antibody or antigen binding fragment thereof that specifically binds to complement control protein domain 18 (CCP18) of factor H (FH), the antibody or fragment comprises the heavy chain CDR1, CDR2, and CDR3 and the light chain CDR1, CDR2, and CDR3, determined under Kabat (see Kabat et al., (1991) Sequences of Proteins of Immunological Interest, NIH Publication No. 91-3242, Bethesda), Chothia (see, e.g., Chothia C & Lesk A M, (1987), J. Mol. Biol. 196: 901-917), MacCallum (see MacCallum R M et al., (1996) J. Mol. Biol. 262: 732-745), or any other CDR determination method known in the art, of the VH and VL sequences of an antibody discloses in Table 1.

In some embodiments, an antibody according to the disclosure is antibody 1. Table 1 provides an overview of the variable heavy and light chain sequences, as well as the individual CDR sequences, of antibody 1. In some embodiments, the antibody or fragment comprises at least one, two, or three of the heavy chain CDR sequences of antibody 1. In some embodiments, the antibody or fragment comprises at least one, two, or three of the light chain CDR sequences of antibody 1. The term "antibody 1" as used herein encompass all antibodies and fragments comprising at least the heavy chain and light chain CDR1, CDR2 and CDR3 region as depicted in Table 1, such as for instance isolated and/or purified antibodies or recombinantly produced antibodies. In some embodiments, antibody 1 competes for binding to the same epitope in CCP18 of FH as antibody FH.07 or antibody FHR-1.3B4.

In some embodiments, an antibody according to the disclosure is antibody 2. Table 1 provides an overview of the variable heavy and light chain sequences, as well as the individual CDR sequences, of antibody 2. In some embodiments, the antibody or fragment comprises at least one, two, or three of the heavy chain CDR sequences of antibody 2. In some embodiments, the antibody or fragment comprises at least one, two, or three of the light chain CDR sequences of antibody 2. The term "antibody 2" as used herein encompass all antibodies and fragments comprising at least the heavy chain and light chain CDR1, CDR2 and CDR3 region as depicted in Table 1, such as for instance isolated and/or purified antibodies or recombinantly produced antibodies. In some embodiments, antibody 2 competes for binding to the same epitope in CCP18 of FH as antibody FH.07 or antibody FHR-1.3B4.

In some embodiments, an antibody according to the disclosure is antibody 3. Table 1 provides an overview of the variable heavy and light chain sequences, as well as the individual CDR sequences, of antibody 3. In some embodiments, the antibody or fragment comprises at least one, two, or three of the heavy chain CDR sequences of antibody 3. In some embodiments, the antibody or fragment comprises at least one, two, or three of the light chain CDR sequences of antibody 3. The term "antibody 3" as used herein encompass all antibodies and fragments comprising at least the heavy chain and light chain CDR1, CDR2 and CDR3 region as depicted in Table 1, such as for instance isolated and/or purified antibodies or recombinantly produced antibodies. In some embodiments, antibody 3 competes for binding to the same epitope in CCP18 of FH as antibody FH.07 or antibody FHR-1.3B4.

In some embodiments, an antibody according to the disclosure is antibody 4. Table 1 provides an overview of the variable heavy and light chain sequences, as well as the individual CDR sequences, of antibody 4. In some embodiments, the antibody or fragment comprises at least one, two, or three of the heavy chain CDR sequences of antibody 4. In some embodiments, the antibody or fragment comprises at least one, two, or three of the light chain CDR sequences of antibody 4. The term "antibody 4" as used herein encompass all antibodies and fragments comprising at least the heavy chain and light chain CDR1, CDR2 and CDR3 region as depicted in Table 1, such as for instance isolated and/or purified antibodies or recombinantly produced antibodies. In some embodiments, antibody 4 competes for binding to the same epitope in CCP18 of FH as antibody FH.07 or antibody FHR-1.3B4.

In some embodiments, the disclosure provides for an isolated, synthetic or recombinant antibody or antigen binding fragment thereof that specifically binds to complement control protein domain 18 (CCP18) of factor H (FH) comprising:
  a light chain CDR1 sequence having the sequence SSVTY (SEQ ID NO: 1) or the sequence TSVTY (SEQ ID NO: 13),
  a light chain CDR2 sequence having the sequence ATS (SEQ ID NO: 2) or the sequence ASS (SEQ ID NO: 14)
  a light chain CDR3 sequence having the sequence QHRSSSNPLT (SEQ ID NO: 3)
  a heavy chain CDR1 having the sequence GFSLTNYG (SEQ ID NO: 5),
  a heavy chain CDR2 having the sequence VWSGGTT (SEQ ID NO: 6) or the sequence of IWSGGTT (SEQ ID NO: 10); and/or
  a heavy chain CDR3 sequence having the sequence ARNFGNYAMDY (SEQ ID NO: 7) or the sequence ARNFGNYAMDF (SEQ ID NO: 11); and/or
  any combinations of the foregoing.

In a particular embodiment, the antibody or fragment comprises:
  a light chain CDR1 sequence having the sequence SSVTY (SEQ ID NO: 1),
  a light chain CDR2 sequence having the sequence ATS (SEQ ID NO: 2),
  a light chain CDR3 sequence having the sequence QHRSSSNPLT (SEQ ID NO: 3),
  a heavy chain CDR1 sequence having the sequence GFSLTNYG (SEQ ID NO: 5),
  a heavy chain CDR2 having the sequence VWSGGTT (SEQ ID NO: 6), and
  a heavy chain CDR3 sequence having the sequence ARNFGNYAMDY (SEQ ID NO: 7).

In a particular embodiment, the antibody or fragment comprises:
  a light chain CDR1 sequence having the sequence SSVTY (SEQ ID NO: 1),
  a light chain CDR2 sequence having the sequence ATS (SEQ ID NO: 2),
  a light chain CDR3 sequence having the sequence QHRSSSNPLT (SEQ ID NO: 3),
  a heavy chain CDR1 sequence having the sequence GFSLTNYG (SEQ ID NO: 5),
  a heavy chain CDR2 having the sequence IWSGGTT (SEQ ID NO: 10), and
  a heavy chain CDR3 sequence having the sequence ARNFGNYAMDF (SEQ ID NO: 11).

In a particular embodiment, the antibody or fragment comprises:
  a light chain CDR1 sequence having the sequence TSVTY (SEQ ID NO: 13),
  a light chain CDR2 sequence having the sequence ASS (SEQ ID NO: 14),
  a light chain CDR3 sequence having the sequence QHRSSSNPLT (SEQ ID NO: 3),
  a heavy chain CDR1 sequence having the sequence GFSLTNYG (SEQ ID NO: 5),
  a heavy chain CDR2 having the sequence VWSGGTT (SEQ ID NO: 6), and
  a heavy chain CDR3 sequence having the sequence ARNFGNYAMDY (SEQ ID NO: 7).

In a particular embodiment, the antibody or fragment comprises:
  a light chain CDR1 sequence having the sequence TSVTY (SEQ ID NO: 13),
  a light chain CDR2 sequence having the sequence ASS (SEQ ID NO: 14),
  a light chain CDR3 sequence having the sequence QHRSSSNPLT (SEQ ID NO: 3),
  a heavy chain CDR1 sequence having the sequence GFSLTNYG (SEQ ID NO: 5),
  a heavy chain CDR2 having the sequence IWSGGTT (SEQ ID NO: 10), and
  a heavy chain CDR3 sequence having the sequence ARNFGNYAMDF (SEQ ID NO: 11).

In some embodiments, the antibody or fragment potentiates FH activity, such as inhibition of alternative complement activation, such as inhibition of hemolytic activity, inhibition of complement component 3 (C3) deposition, and/or an increase of binding of FH to C3b, iC3b and/or C3d. In some embodiments, the fragment comprises at least a heavy chain variable domain (VH) and/or a light chain variable domain (VL). In some embodiments, a fragment comprises at least a Fab fragment.

In some embodiments, the antibody or fragment has a binding affinity for FH with a $K_D$ of $2.5 \times 10^{-8}$ M or less and/or a binding affinity for a FH fragment comprised of CCP18-20 with a $K_D$ of $0.1 \times 10^{-9}$ M or less, such as an antibody or fragment that has a binding affinity for FH with a $K_D$ of $1.25 \times 10^{-8}$ M or less and/or a binding affinity for a FH fragment comprised of CCP18-20 with a $K_D$ of $0.04 \times 10^{-9}$ M or less.

In a further embodiment, the disclosure provides an isolated, synthetic or recombinant antibody or antigen binding fragment thereof that specifically binds to CCP18 of FH comprising a light chain CDR1 sequence having the sequence SSVTY (SEQ ID NO: 1), a light chain CDR2 sequence having the sequence ATS (SEQ ID NO: 2) and a light chain CDR3 having the sequence QHRSSSNPLT (SEQ ID NO: 3), a heavy chain CDR1 having the sequence GFSLTNYG (SEQ ID NO: 5), a heavy chain CDR2 having the sequence VWSGGTT (SEQ ID NO: 6), and a heavy chain CDR3 sequence having the sequence ARNFGNYAMDY (SEQ ID NO: 7). In one embodiment, the antibody or fragment comprises a variable light chain sequence comprising a sequence which has at least 80%, at least 85%, at least 90%, at least 91%, at least 92%, at least 93%, at least 94%, at least 95%, at least 96%, at least 97%, at least 98%, at least 99%, or 100% sequence identity to the sequence SEQ ID NO: 4. In some embodiments, the antibody comprises a variable heavy chain sequence comprising a sequence which has at least 80%, at least 85%, at least 90%, at least 91%, at least 92%, at least 93%, at least 94%, at least 95%, at least 96%, at least 97%, at least 98%, at least 99%, or 100% sequence identity to the sequence SEQ ID NO: 8. In a particular embodiment, the antibody or fragment comprises a variable light chain sequence comprising the sequence of SEQ ID NO: 4 and a variable heavy chain sequence comprising the sequence of SEQ ID NO: 8. In some embodiments, the antibody or fragment potentiates FH activity, such as inhibition of alternative complement activation, such as inhibition of hemolytic activity, inhibition of complement component 3 (C3) deposition, and/or an increase of binding of FH to C3b, iC3b and/or C3d. In some embodiments, the fragment comprises at least a heavy chain variable domain (VH) and/or a light chain variable domain (VL). In some embodiments, the fragment comprises at least a Fab fragment.

In a further embodiment, the disclosure provides an isolated, synthetic or recombinant antibody or antigen binding fragment thereof that specifically binds to CCP18 of FH comprising a light chain CDR1 sequence having the sequence SSVTY (SEQ ID NO: 1), a light chain CDR2 sequence having the sequence ATS (SEQ ID NO: 2) and a light chain CDR3 having the sequence QHRSSSNPLT (SEQ ID NO: 3), a heavy chain CDR1 having the sequence GFSLTNYG (SEQ ID NO: 5), a heavy chain CDR2 having the sequence IWSGGTT (SEQ ID NO: 10), and a heavy chain CDR3 sequence having the sequence ARNFGNYAMDF (SEQ ID NO: 11). In one embodiment, the antibody or fragment comprises a variable light chain sequence comprising a sequence which has at least 80%, at least 85%, at least 90%, at least 91%, at least 92%, at least 93%, at least 94%, at least 95%, at least 96%, at least 97%, at least 98%, at least 99%, or 100% sequence identity to the sequence SEQ ID NO: 4. In some embodiments, the antibody or fragment comprises a variable heavy chain sequence comprising a sequence which has at least 80%, at least 85%, at least 90%, at least 91%, at least 92%, at least 93%, at least 94%, at least 95%, at least 96%, at least 97%, at least 98%, at least 99%, or 100% sequence identity to the sequence SEQ ID NO: 12. In a particular embodiment, the antibody or fragment comprises a variable light chain sequence comprising the sequence of SEQ ID NO: 4 and a variable heavy chain sequence comprising the sequence of SEQ ID NO: 12. In some embodiments, the antibody or fragment potentiates FH activity, inhibition of alternative complement activation, such as inhibition of hemolytic activity, inhibition of complement component 3 (C3) deposition, and/or an increase of binding of FH to C3b, iC3b and/or C3d. In some embodiments, the fragment comprises at least a heavy chain variable domain (VH) and/or a light chain variable domain (VL). In some embodiments, the fragment comprises at least a Fab fragment.

In a further embodiment, the disclosure provides an isolated, synthetic or recombinant antibody or antigen binding fragment thereof that specifically binds to CCP18 of FH comprising a light chain CDR1 sequence having the sequence TSVTY (SEQ ID NO: 13), a light chain CDR2 sequence having the sequence ASS (SEQ ID NO: 14) and a light chain CDR3 having the sequence QHRSSSNPLT (SEQ ID NO: 3), a heavy chain CDR1 having the sequence GFSLTNYG (SEQ ID NO: 5), a heavy chain CDR2 having the sequence VWSGGTT (SEQ ID NO: 6), and a heavy chain CDR3 sequence having the sequence ARNFGNYAMDY (SEQ ID NO: 7). In one embodiment, said antibody or fragment comprises a variable light chain sequence comprising a sequence which has at least 80%, at least 85%, at least 90%, at least 91%, at least 92%, at least 93%, at least 94%, at least 95%, at least 96%, at least 97%, at least 98%, at least 99%, or 100% sequence identity to the sequence SEQ ID NO: 16. In some embodiments, the antibody or fragment comprises a variable heavy chain sequence comprising a sequence which has at least 80%, at least 85%, at least 90%, at least 91%, at least 92%, at least 93%, at least 94%, at least 95%, at least 96%, at least 97%, at least 98%, at least 99%, or 100% sequence identity to the sequence SEQ ID NO: 8. In a particular embodiment, the antibody or fragment comprises a variable light chain sequence comprising the sequence of SEQ ID NO: 16 and a variable heavy chain sequence comprising the sequence of SEQ ID NO: 8. In some embodiments, the antibody or fragment potentiates FH activity, such as inhibition of alternative complement activation, such as inhibition of hemolytic activity, inhibition of complement component 3 (C3) deposition, and/or an increase of binding of FH to C3b, iC3b and/or C3d. In some embodiments, the fragment comprises at least a heavy chain variable domain (VH) and/or a light chain variable domain (VL). In some embodiments, the fragment comprises at least a Fab fragment.

In a further embodiment, the disclosure provides an isolated, synthetic or recombinant antibody or antigen binding fragment thereof that specifically binds to CCP18 of FH comprising a light chain CDR1 sequence having the sequence TSVTY (SEQ ID NO: 13), a light chain CDR2 sequence having the sequence ASS (SEQ ID NO: 14) and a light chain CDR3 having the sequence QHRSSSNPLT (SEQ ID NO: 3), a heavy chain CDR1 having the sequence GFSLTNYG (SEQ ID NO: 5), a heavy chain CDR2 having the sequence IWSGGTT (SEQ ID NO: 10), and a heavy chain CDR3 sequence having the sequence ARNFGNYAMDF (SEQ ID NO: 11). In one embodiment, the antibody or fragment comprises a variable light chain sequence comprising a sequence which has at least 80%, at least 85%, at least 90%, at least 91%, at least 92%, at least 93%, at least 94%, at least 95%, at least 96%, at least 97%, at least 98%, at least 99%, or 100% sequence identity to the sequence SEQ ID NO: 16. In some embodiments, the antibody or fragment comprises a variable heavy chain sequence comprising a sequence which has at least 80%, at least 85%, at least 90%, at least 91%, at least 92%, at least 93%, at least 94%, at least 95%, at least 96%, at least 97%, at least 98%, at least 99%, or 100% sequence identity to the sequence SEQ ID NO: 12. In a particular embodiment, the antibody or fragment comprises a variable light chain sequence comprising the sequence of SEQ ID NO: 16 and a variable heavy chain sequence comprising the sequence of SEQ ID NO: 12. In some embodiments, the antibody or fragment potentiates FH activity, such as inhibition of alternative complement activation, such as inhibition of hemolytic activity, inhibition of complement component 3 (C3) deposition, and/or an increase of binding of FH to C3b, iC3b and/or C3d. In some embodiments, the fragment comprises at least a heavy chain variable domain (VH) and/or a light chain variable domain (VL). In some embodiments, the fragment comprises at least a Fab fragment.

In some embodiments, any of the antibodies or fragments disclosed herein has a binding affinity for FH with a $K_D$ of $2.5 \times 10^{-8}$ M or less and/or a binding affinity for a FH fragment comprised of CCP18-20 with a $K_D$ of $0.1 \times 10^{-9}$ M or less. In some embodiments, the antibody or fragment has a binding affinity for FH with a $K_D$ of 22.5 nM or less, 20 nM or less, 17.5 nM or less, 15 nM or less, 12.5 nM or less, 10 nM or less, 9 nM or less, 8 nM or less, 7 nM or less, 6 nM or less, 5 nM or less, 4 nM or less, 3 nM or less, 2 nM or less, 1 nM or less, 0.9 nM or less, 0.8 nM or less, 0.7 nM or less, or 0.6 nM or less, and/or a binding affinity for a FH fragment comprised of CCP18-20 with a $K_D$ of $0.09 \times 10^{-9}$ M or less, $0.08 \times 10$ M or less, $0.07 \times 10^{-9}$ M or less, $0.06 \times 10^{-9}$ M or less, $0.05 \times 10^{-9}$ M or less, $0.04 \times 10^{-9}$ M or less, $0.03 \times 10^{-9}$ M or less, $0.02 \times 10^{-9}$ M or less, $1 \times 10^{-11}$ M or less, $0.9 \times 10^{-11}$ M or less, $0.8 \times 10^{-11}$ M or less, $0.7 \times 10^{-11}$ M or less, or $0.6 \times 10^{-11}$ M or less.

In some embodiments, any of the antibodies or fragments disclosed herein inhibits C3 deposition on LPS in vitro in the presence of 10% (v/v) normal human serum with an $IC_{50}$ value of 38 nM or less. In some embodiments, the antibody or fragment inhibits C3 deposition on LPS in vitro in the presence of 10% (v/v) normal human serum with an $IC_{50}$ value of 35 nM or less, 32 nM or less, 30 nM or less, 28 nM or less, 25 nM or less, 23 nM or less, 20 nM or less, 18 nM or less, 15 nM or less or 10 nM or less. In some embodiments, an antibody or fragment thereof according to the disclosure inhibits C3 deposition on LPS in vitro in the presence of 10% (v/v) normal human serum with an $IC_{50}$ value of between 15 nM and 30 nM.

In some embodiments, any of the antibodies or fragments disclosed herein inhibits hemolytic activity in vitro in the presence of 10% (v/v) normal human serum with an $IC_{50}$ value of 150 nM or less. In some embodiments, the antibody or fragment inhibits hemolytic activity in vitro in the presence of 10% (v/v) normal human serum with an $IC_{50}$ value of 105 nM or less. In some embodiments, an antibody or fragment thereof according to the disclosure inhibits hemolytic activity in vitro in the presence of 10% (v/v) normal human serum with an $IC_{50}$ value of 150 nM or less, 130 nM or less, 115 nM or less, 105 nM or less, 100 nM or less, 95 nM or less, 75 nM or less, 70 nM or less, 65 nM or less or 60 nM or less. In some embodiments, an antibody or fragment thereof according to the disclosure inhibits hemolytic activity in vitro in the presence of 10% (v/v) normal human serum with an $IC_{50}$ value between 60 nM and 80 nM.

In some embodiments, any of the antibodies or fragments disclosed herein increases binding affinity ($K_D$) of FH for C3b in vitro to 2 µM or less, 1.5 µM or less, 1 µM or less, 500 nM or less, 400 nM or less, or 300 nM or less and/or increases binding affinity of FH for C3b in vitro at least 2.5 times, 3 times, 3.5 times, 4 times, 4.5 times or 5 times. In some embodiments, any of the antibodies or fragments disclosed herein increases binding affinity ($K_D$) of FH for C3b in vitro to between 50-500 nM. In some embodiments, any of the antibodies or fragments disclosed herein increases binding affinity ($K_D$) of FH for C3b in vitro to between 50-300 nM. In some embodiments, any of the antibodies or fragments disclosed herein increases binding affinity ($K_D$) of FH for C3b in vitro to between 100-300 nM. In some embodiments, any of the antibodies or fragments disclosed herein increases binding affinity ($K_D$) of FH for C3b in vitro to between 250-300 nM.

Optionally, the sequence of at least one of any one or more of the CDRs disclosed herein is optimized, thereby generating a variant antibody or fragment, for instance to (further) improve binding affinity, selectivity, FH potentiating ability and/or in vivo or storage stability. In some embodiments, antibodies or fragments according to the disclosure have a high storage stability, in particular an improved storage stability as compared to antibody FH.07 or antibody FHR-1.3B4. In some embodiments, antibodies or fragments according to the disclosure have a high in vivo stability, in particular an improved in vivo stability as compared to antibody FH.07 or antibody FHR-1.3B4. In some embodiments, antibodies or fragments according to the disclosure have a high selectivity, in particular an increased selectivity as compared to antibody FH.07 or antibody FHR-1.3B4.

In addition, optionally at least one sequence in at least one of the framework regions of an antibody or fragment of the disclosure is optimized, for instance to improve binding efficacy or stability of the antibody or fragment or to reduce side-effects of non-human sequences after administration thereof to a human. This is for instance done by mutagenesis procedures. A skilled person is capable of generating antibody variants comprising at least one altered CDR or framework sequence. CDR and/or framework sequences are for instance optimized by mutating a nucleic acid encoding such framework sequence. For instance, conservative amino acid substitution is applied. In some embodiments, any of the CDR, framework, variable heavy chain, variable light chain sequences disclosed herein comprises at least 1, 2, 3, 4, 5, 6, 7, 8, 9, 10, 11, 12, 13, 14, 15, 16, 17, 18, 19 or 20 amino acid substitutions, deletions, or insertions (e.g., conservative substitutions) as compared to any one or more of the amino acid sequences disclosed herein. In some embodiments, any of the CDR, framework, variable heavy chain, variable light chain sequences disclosed herein comprises at least 1, 2, 3, 4, or 5 amino acid substitutions, deletions, or insertions (e.g., conservative substitutions) as compared to any one or more of the amino acid sequences disclosed herein. In some embodiments, any of the CDR, framework, variable heavy chain, variable light chain sequences disclosed herein comprises no more than 1, 2, 3, 4, 5, 6, 7, 8, 9, 10, 11, 12, 13, 14, 15, 16, 17, 18, 19 or 20 amino acid substitutions, deletions, or insertions (e.g., conservative substitutions) as compared to any one or more of the amino acid sequences disclosed herein. In some embodiments, any of the CDR, framework, variable heavy chain, variable light chain sequences disclosed herein comprises no more than 1, 2, 3, 4, or 5 amino acid substitutions, deletions, or insertions (e.g., conservative substitutions) as compared to any one or more of the amino acid sequences disclosed herein. Examples of conservative amino acid substitution include the substitution of one hydrophobic residue such as isoleucine, valine, leucine or methionine for another hydrophobic residue, and the substitution of one polar residue for another polar residue, such as the substitution of arginine for lysine, glutamic acid for aspartic acid, or glutamine for asparagine.

In order to select an improved antibody or fragment, the binding affinity, FH potentiating ability and/or stability of the resulting variant antibodies or fragments may be tested, e.g. using test described herein. Once antibodies or fragments specific for FH, in particular for CCP18 of FH, have been obtained, the desired biological activity thereof, i.e. their ability to potentiate the activity of FH, can be tested by several methods known to the skilled person. As described herein before, potentiating the activity of FH may encompass inhibition of hemolytic activity, inhibition of C3 deposition on cells, and/or an increase of binding of FH to C3b. Functional assays to test these activities are described herein before and detailed in the Examples. Typically, up to three amino acid residues of a CDR sequence may vary while retaining the same specificity, depending on the number of amino acids the CDR is composed of. Hence, in some embodiments, an antibody or fragment according to the disclosure contains a heavy chain and light chain CDR1, CDR2 and CDR3 sequence wherein at most 3, at most 2, or at most 1 amino acid of each CDR is varied as compared to the heavy and light chain CDR1, CDR2 and CDR3 sequences of Table 1. In some embodiments, the antibody or fragment comprises a light chain CDR3 and a heavy chain CDR3 of the same antibody as depicted in Table 1, a light chain CDR2 of the antibody wherein at most 1 amino acid is varied, and a light chain CDR1, heavy chain CDR1 and heavy chain CDR2 wherein at most 3 amino acids are varied. In some embodiments, the antibody or fragment comprises a light chain CDR2 and CDR3 and a heavy chain CDR3 of the same antibody as depicted in Table 1, and a light chain CDR1, heavy chain CDR1 and heavy chain CDR2 wherein at most 2 amino acids, or at most 1 amino acid, are varied.

The disclosure therefore further provides an isolated, synthetic or recombinant antibody or fragment thereof that specifically binds to complement control protein domain 18 (CCP18) of factor H (FH) comprising:

a light chain CDR1 sequence having a sequence which is at least 60% or at least 80% identical to the sequence SSVTY (SEQ ID NO: 1), a light chain CDR2 sequence having a sequence which is at least 60% identical to the sequence ATS (SEQ ID NO: 2), and a light chain CDR3 having a sequence which is at least 60%, at least 70%, at least 80%, or at least 90% identical to the sequence QHRSSSNPLT (SEQ ID NO: 3), a heavy chain CDR1 having a sequence which is at least 60%, at least 70%, at least 80%, or at least 90% identical to the sequence GFSLTNYG (SEQ ID NO: 5), a heavy chain CDR2 having a sequence which is at least 60%, at least 70%, at least 80%, or at least 90% identical to the sequence VWSGGTT (SEQ ID NO: 6), and a heavy chain CDR3 sequence having a sequence which is at least 60%, at least 70%, at least 80%, or at least 90% identical to the sequence ARNFGNYAMDY (SEQ ID NO: 7), a light chain CDR1 sequence having a sequence which is at least 60% or at least 80% identical to the sequence SSVTY (SEQ ID NO: 1), a light chain CDR2 sequence having a sequence that is at least 60% identical to the sequence ATS (SEQ ID NO: 2), and a light chain CDR3 having a sequence which is at least 60%, at least 70%, at least 80%, or at least 90% identical to the sequence QHRSSSNPLT (SEQ ID NO: 3), a heavy chain CDR1 having a sequence which is at least 60%, at least 70%, at least 80%, or at least 90% identical to the sequence GFSLTNYG (SEQ ID NO: 5), a heavy chain CDR2 having a sequence which is at least 60%, at least 70%, at least 80%, or at least 90% identical to the sequence IWSGGTT (SEQ ID NO: 10), and a heavy chain CDR3 sequence having a sequence which is at least 60%, at least 70%, at least 80%, or at least 90% identical to the sequence ARNFGNYAMDF (SEQ ID NO: 11), a light chain CDR1 sequence having a sequence which is at least 60% or at least 80% identical to the sequence TSVTY (SEQ ID NO: 13), a light chain CDR2 sequence having a sequence that is at least 60% identical to the ASS (SEQ ID NO: 14), and a light chain CDR3 having a sequence which is at least 60%, at least 70%, at least 80%, or at least 90% identical to the sequence QHRSSSNPLT (SEQ ID NO: 3), a heavy chain CDR1 having a sequence which is at least 60%, at least 70%, at least 80%, or at least 90% identical to the sequence GFSLTNYG (SEQ ID NO: 5), a heavy chain CDR2 having a sequence which is at least 60%, at least 70%, at least 80%, or at least 90% identical to the sequence VWSGGTT (SEQ ID NO: 6), and a heavy chain CDR3 sequence having a sequence which is at least 60%, at least 70%, at least 80%, or at least 90% identical to the sequence ARNFGNYAMDY (SEQ ID NO: 7), a light chain CDR1 sequence having a sequence which is at least 60% or at least 80% identical to the sequence TSVTY (SEQ ID NO: 13), a light chain CDR2 sequence having a sequence that is at least 60% identical to the ASS (SEQ ID NO: 14), and a light chain CDR3 having a sequence which is at least 60%, at least 70%, at least 80%, or at least 90% identical to the sequence of QHRSSSNPLT (SEQ ID NO: 3), a heavy chain CDR1 having a sequence which is at least 60%, at least 70%, at least 80%, or at least 90% identical to the sequence GFSLTNYG (SEQ ID NO: 5), a heavy chain CDR2 having a sequence which is at least 60%, at least 70%, at least 80%, or at least 90% identical to the sequence IWSGGTT (SEQ ID NO: 10), and a heavy chain CDR3 sequence having a sequence which is at least 60%, at least 70%, at least 80%, or at least 90% identical to the sequence ARNFGNYAMDF (SEQ ID NO: 11).

In some embodiments, the antibody or fragment potentiates FH activity. In some embodiments, the antibody or fragment comprises heavy chain CDR1, CDR2 and/or CDR3 sequences and/or light chain CDR1, CDR2 and/or CDR3 sequences that are at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, identical to the indicated sequences.

The disclosure further provides an isolated, synthetic or recombinant antibody or fragment thereof that specifically binds to complement control protein domain 18 (CCP18) of factor H (FH) comprising:

a light chain CDR1 sequence having a sequence SSVTY (SEQ ID NO: 1) optionally having 1 amino acid substitution, a light chain CDR2 sequence having a sequence ATS (SEQ ID NO: 2) and a light chain CDR3 having a sequence QHRSSSNPLT (SEQ ID NO: 3) optionally having 1 or 2 amino acid substitutions, a heavy chain CDR1 having a sequence GFSLTNYG (SEQ ID NO: 5) optionally having 1 or 2 amino acid substitutions, a heavy chain CDR2 having a sequence VWSGGTT (SEQ ID NO: 6) optionally having 1 or 2 amino acid substitutions, and a heavy chain CDR3 sequence ARNFGNYAMDY (SEQ ID NO: 7) optionally having 1 or 2 amino acid substitutions;

a light chain CDR1 sequence having a sequence SSVTY (SEQ ID NO: 1) optionally having 1 amino acid substitution, a light chain CDR2 sequence having a sequence ATS (SEQ ID NO: 2) and a light chain CDR3 having a sequence QHRSSSNPLT (SEQ ID NO: 3) optionally having 1 or 2 amino acid substitutions, a heavy chain CDR1 having a sequence GFSLTNYG (SEQ ID NO: 5) optionally having 1 or 2 amino acid substitutions, a heavy chain CDR2 having a sequence IWSGGTT (SEQ ID NO: 10) optionally having 1 or 2 amino acid substitutions, and a heavy chain CDR3 sequence ARNFGNYAMDF (SEQ ID NO: 11) optionally having 1 or 2 amino acid substitutions;

a light chain CDR1 sequence having a sequence TSVTY (SEQ ID NO: 13) optionally having 1 or 2 amino acid substitutions, a light chain CDR2 sequence ASS (SEQ ID NO: 14) and a light chain CDR3 having a sequence QHRSSSNPLT (SEQ ID NO: 3) optionally having 1 or 2 amino acid substitutions, a heavy chain CDR1 having a sequence GFSLTNYG (SEQ ID NO: 5) optionally having 1 or 2 amino acid substitutions, a heavy chain CDR2 having a sequence VWSGGTT (SEQ ID NO: 6) optionally having 1 or 2 amino acid substitutions, and a heavy chain CDR3 ARNFGNYAMDY (SEQ ID NO: 7) optionally having 1 or 2 amino acid substitutions; or a light chain CDR1 sequence having a sequence TSVTY (SEQ ID NO: 13) optionally having 1 amino acid substitution, a light chain CDR2 sequence having a sequence ASS (SEQ ID NO: 14) and a light chain CDR3 having a sequence QHRSSSNPLT (SEQ ID NO:

3) optionally having 1 or 2 amino acid substitutions, a heavy chain CDR1 having a sequence GFSLTNYG (SEQ ID NO: 5) optionally having 1 or 2 amino acid substitutions, a heavy chain CDR2 having a sequence IWSGGTT (SEQ ID NO: 10) optionally having 1 or 2 amino acid substitutions, and a heavy chain CDR3 sequence having a sequence ARNFGNYAMDF (SEQ ID NO: 11) optionally having 1 or 2 amino acid substitutions.

In some embodiments, any of the antibodies or antigen-binding fragments disclosed herein comprise at least one or more CDR(s) from any of the heavy or light chain sequences disclosed herein. In some embodiments, any of the antibodies or antigen-binding fragments disclosed herein comprise at least one or more CDR(s) from any of the variable heavy or variable light chain sequences of SEQ ID NOs: 4, 8, 12, or 16. In some embodiments, any of the antibodies or antigen-binding fragments disclosed herein comprise at least one or more CDR from any of the heavy or light chain sequences disclosed herein, wherein the CDR is determined using the Kabat system. In some embodiments, any of the antibodies or antigen-binding fragments disclosed herein comprise at least one or more CDR from any of the heavy or light chain sequences disclosed herein, wherein the CDR is determined using the Chothia system. In some embodiments, any of the antibodies or antigen-binding fragments disclosed herein comprise at least one or more CDR from any of the heavy or light chain sequences disclosed herein, wherein the CDR is determined using the MacCallum system. In some embodiments, any of the antibodies or antigen-binding fragments disclosed herein comprise at least one or more CDR from any of the heavy or light chain sequences disclosed herein, wherein the CDR is determined using the AbM system. In some embodiments, any of the antibodies or antigen-binding fragments disclosed herein comprise at least one or more CDR from any of the heavy or light chain sequences disclosed herein, wherein the CDR is determined using the IMGT system.

The system described by Kabat, also referred to as "numbered according to Kabat," "Kabat numbering," "Kabat definitions," and "Kabat labeling," provides an unambiguous residue numbering system applicable to any variable domain of an antibody, and provides precise residue boundaries defining the three CDRs of each chain. (Kabat et al., Sequences of Proteins of Immunological Interest, National Institutes of Health, Bethesda, Md. (1987) and (1991), the contents of which are incorporated by reference in their entirety. These CDRs are referred to as Kabat CDRs and comprise about residues 24-34 (CDR1), 50-56 (CDR2) and 89-97 (CDR3) in the light chain variable domain, and 31-35 (CDR1), 50-65 (CDR2) and 95-102 (CDR3) in the heavy chain variable domain. When the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. The "EU index as in Kabat" refers to the residue numbering of the human IgG1 EU antibody.

Other CDR numbering systems are also used in the art. Chothia and coworkers found that certain sub-portions within Kabat CDRs adopt nearly identical peptide backbone conformations, despite having great diversity at the level of amino acid sequence. (Chothia et al. (1987) J. Mol. Biol. 196: 901-917; and Chothia et al. (1989) Nature 342: 877-883). These sub-portions were designated as L1, L2, and L3 or H1, H2, and H3 where the "L" and the "H" designates the light chain and the heavy chains regions, respectively. These CDRs can be referred to as "Chothia CDRs," "Chothia numbering," or "numbered according to Chothia," and comprise about residues 24-34 (CDR1), 50-56 (CDR2) and 89-97 (CDR3) in the light chain variable domain, and 26-32 (CDR1), 52-56 (CDR2) and 95-102 (CDR3) in the heavy chain variable domain. Mol. Biol. 196:901-917 (1987).

The system described by MacCallum, also referred to as "numbered according to MacCallum," or "MacCallum numbering" comprises about residues 30-36 (CDR1), 46-55 (CDR2) and 89-96 (CDR3) in the light chain variable domain, and 30-35 (CDR1), 47-58 (CDR2) and 93-101 (CDR3) in the heavy chain variable domain. MacCallum et al. ((1996) J. Mol. Biol. 262(5):732-745).

The system described by AbM, also referred to as "numbering according to AbM," or "AbM numbering" comprises about residues 24-34 (CDR1), 50-56 (CDR2) and 89-97 (CDR3) in the light chain variable domain, and 26-35 (CDR1), 50-58 (CDR2) and 95-102 (CDR3) in the heavy chain variable domain.

The IMGT (INTERNATIONAL IMMUNOGENETICS INFORMATION SYSTEM) numbering of variable regions can also be used, which is the numbering of the residues in an immunoglobulin variable heavy or light chain according to the methods of the IIMGT, as described in Lefranc, M.-P., "The IMGT unique numbering for immunoglobulins, T cell Receptors and Ig-like domains", The Immunologist, 7, 132-136 (1999), and is expressly incorporated herein in its entirety by reference. As used herein, "IMGT sequence numbering" or "numbered according to IMTG," refers to numbering of the sequence encoding a variable region according to the IMGT. For the heavy chain variable domain, when numbered according to IMGT, the hypervariable region ranges from amino acid positions 27 to 38 for CDR1, amino acid positions 56 to 65 for CDR2, and amino acid positions 105 to 117 for CDR3. For the light chain variable domain, when numbered according to IMGT, the hypervariable region ranges from amino acid positions 27 to 38 for CDR1, amino acid positions 56 to 65 for CDR2, and amino acid positions 105 to 117 for CDR3. In some embodiments of the constructs and antigen-binding arms described herein, the CDRs recited herein comprise about residues 24-34 (CDR1), 49-56 (CDR2) and 89-97 (CDR3) in the light chain variable domain, and 27-35 (CDR1), 49-60 (CDR2) and 93-102 (CDR3) in the heavy chain variable domain, when numbered according to Chothia numbering. In some embodiments, CDR2 in the light chain variable domain can comprise amino acids 49-56, when numbered according to Chothia numbering.

Antibodies or fragments thereof according to the disclosure are in some embodiments monoclonal antibodies or fragments. A monoclonal antibody is an antibody consisting substantially of a single molecular species. Monoclonal antibodies are obtained from a population of homogeneous antibodies, having the same sequence and binding the same epitope, with the exception of possible variant antibodies or fragments that have one or more mutations that have occurred spontaneously, e.g., during production. Monoclonal antibodies can be advantageously produced recombinantly so that amounts of the antibody can be obtained that are significantly higher than that of polyclonal antibodies present in an antiserum. However, polyclonal antibodies and fragments are also encompassed by the disclosure. In some embodiments, an antibody or fragment according to the present disclosure is a chimeric or humanized antibody. In some embodiments, the antibody or fragment thus comprises at least human light chain and heavy chain constant regions. In some embodiments, the antibody or fragment also comprises human framework regions in the heavy and light chain variable regions. In some embodiments, human antibodies or fragments are provided, which consist entirely of human sequences. In some embodiments, the use of chimeric, humanized or human antibodies is desirable over the use of non-human antibodies because the use of non-human antibodies or fragments for treatment of human diseases is hampered by a number of factors. The human body may recognize non-human antibodies as foreign, which will result in an immune response against the non-human antibodies or fragments, resulting in adverse side effects and/or rapid clearance of the antibodies or fragments from the circulation. The chance of side-effects is reduced when chimeric, humanized or human antibodies are administered to humans. In addition, generally a longer half-life in the circulation is achieved when chimeric, humanized or human antibodies are used because of reduced clearance when compared to non-human antibodies. In some embodiments, human germline sequences are used for framework regions in antibodies or fragments according to the disclosure. The use of human germline sequences minimizes the risk of immunogenicity of the antibodies or fragments, because these sequences are less likely to contain somatic alterations which are unique to individuals from which the framework regions are derived, and may cause an immunogenic response when applied to another human individual.

Procedures for humanization of antibodies or the provide chimeric antibodies are well known in the art. Various recombinant DNA-based approaches have been established that are aimed at increasing the content of amino acid residues in antibodies that also occur at the same of similar position in human antibodies while retaining the specificity and affinity of the parental non-human antibody. For example, the framework regions of the variable regions of mouse antibodies are substituted by the corresponding human framework regions having the highest degree of homology, leaving the non-human CDR intact. Further methods suitable for humanizing antibodies according to the disclosure include, but are not limited to, grafting of CDRs (Queen, C et. al. 1989; Carter, P et al. 1992); resurfacing (Padlan, E A, et. al. 1991), superhumanization (Tan, P D A, et. al. 2002), human string content optimization (Lazar, G. A. et. al. 2007) and humaneering (Almagro, J C, et. al. 2008).

In one embodiment, an antibody or fragment according to the disclosure is a multispecific antibody, such as a bispecific antibody. Multispecific antibodies are monoclonal antibodies that have binding specificities for at least two different antigens and/or epitopes. In one embodiment, a bispecific antibody has binding specificity for FH, e.g., comprising one variable light chain and at one variable heavy chain that specifically binds to CCP18 of FH as described herein, and has binding specificity for another antigen. In another embodiments, bispecific antibodies may bind to two different epitopes of FH.

An antibody or fragment according to the disclosure can be of any class. The "class" of an antibody refers to the type of constant domain or constant region possessed by its heavy chain. There are five major classes of antibodies: IgA, IgD, IgE, IgG, and IgM, some of which can be further divided into subclasses or isotypes, such as IgG1, IgG2, IgG3 and IgG4. In certain embodiments, an antibody according to the disclosure comprises the constant region (e.g., Fc domain) of an IgG (e.g., IgG1, IgG2, IgG3, or IgG4). In certain embodiments, an antibody according to the disclosure comprises the constant region (e.g., Fc domain) of a human IgG (e.g., human IgG1, IgG2, IgG3, or IgG4). The Fc domain mediates the effector functions of an antibody, including the ability to induce antibody-dependent cellular cytotoxicity (ADCC) and complement-dependent cytotoxicity (CDC). In certain embodiments, the antibody disclosed herein comprises an Fc domain having one or more mutations that reduces an effector function of the Fc. In some embodiments, the antibody disclosed herein comprises an Fc domain comprising a mutation (e.g., substitution relative to wild-type human IgG1) at one or more of positions selected from 234, 235, 236, 237, 270, 297, 318, 320, 322, 329, and 331. Such mutations are known in the art and include without limitation L234A, L235A, G237A, P329A or P329G, A330S, P331S, N297Q, N297A, and combinations thereof. The Fc domain also binds the neonatal Fc receptor FcRn, thereby facilitating recycling of the antibody and thereby increasing the antibody's half-life. In certain embodiments, the antibody disclosed herein comprises an Fc domain having one or more mutations that increases the binding affinity of the Fc to FcRn. Such mutations are known in the art and include without limitation M252Y/T256D, T256D/T307Q, and T256D/T307W.

In certain embodiments, any of the antibodies or fragments disclosed herein may further comprise post-translational modifications in addition to any that are naturally present in the native antibodies or fragments. Such modifications include, but are not limited to, acetylation, carboxylation, glycosylation, phosphorylation, lipidation, pegylation (polyethylene glycol) and acylation. As a result, the modified polypeptides may contain non-amino acid elements, such as polyethylene glycols, lipids, mono- or polysaccharides, and phosphates. In particular embodiments, the antibody or fragment is PEGylated. In further particular embodiments, the antibody or fragment is a PEGylated Fab molecule.

Antibodies specific for a particular antigen, such as FH in accordance with the present disclosure, can be prepared by various methods known in the art. For instance, human FH can be used as an immunogen for eliciting antibodies. As another example, the CCP18 domain of human FH of a FH related protein can be used as an immunogen. One example of such method is by immunization and hybridoma generation as described in the Examples. Mouse monoclonal antibodies to FH can for instance be generated by immunizing mice, e.g. BALB/c mice, intraperitoneally with human factor H or a FH related protein such as FHR-1, optionally in the presence of an adjuvant, such as montanide, for instance at four week intervals. Several days after the fourth immunization, spleen cells can be fused with e.g. the myeloma cell line SP2/0. The presence of factor H specific antibodies in the supernatants of the hybridomas can be tested by ELISA. For instance, microtiterplates are coated with a moAb (e.g. rat anti-mouse kappa moAb RM19) to capture mouse IgG antibodies. Specificity of the antibodies may be determined by biotinylated factor H. Another example of a method to provide FH-specific antibodies is by screening phage display libraries expressing recombinant nucleic acid sequences encoding immunoglobulin chains. Methods for antibody phage display have been used in the art and described extensively. Screening of the library for antibodies can be performed with the same antigen used for immunization, e.g. human FH, a FH related protein or the CCP18 domain of human FH.

C. Nucleic Acids and Vectors

The disclosure further provides one or more isolated, synthetic or recombinant nucleic acids comprising a nucleic acid sequence encoding any of the antibodies or fragments thereof disclosed herein. In some embodiments, the nucleic acids encode at least the heavy chain CDR1, CDR2 and CDR3 and/or the light chain CDR1, CDR2 and CDR3 of Antibody 1 as depicted in Table 1. In some embodiments, the nucleic acids encode at least the heavy chain CDR1, CDR2 and CDR3 and/or the light chain CDR1, CDR2 and CDR3 of Antibody 2 as depicted in Table 1. In some embodiments, the nucleic acids encode at least the heavy chain CDR1, CDR2 and CDR3 and/or the light chain CDR1, CDR2 and CDR3 of antibody Antibody 3 as depicted in Table 1. In some embodiments, the nucleic acids encode at least the heavy chain CDR1, CDR2 and CDR3 and/or the light chain CDR1, CDR2 and CDR3 of Antibody 4 as depicted in Table 1.

In some embodiments, a nucleic acid according to the disclosure has a length of at least 30 nucleotides, at least 50 nucleotides, or at least 75 nucleotides. In some embodiments, a nucleic acid according to the disclosure encodes a monoclonal chimeric or humanized antibody or fragment thereof comprising the heavy chain CDR sequences and light chain CDR sequences and/or the heavy chain variable region and the light chain variable region of Antibody 1. In some embodiments, a nucleic acid according to the disclosure encodes a monoclonal chimeric or humanized antibody or fragment thereof comprising the heavy chain CDR sequences and light chain CDR sequences and/or the heavy chain variable region and the light chain variable region of Antibody 2. In some embodiments, a nucleic acid according to the disclosure encodes a monoclonal chimeric or humanized antibody or fragment thereof comprising the heavy chain CDR sequences and light chain CDR sequences and/or the heavy chain variable region and the light chain variable region of Antibody 3. In some embodiments, a nucleic acid according to the disclosure encodes a monoclonal chimeric or humanized antibody or fragment thereof comprising the heavy chain CDR sequences and light chain CDR sequences and/or the heavy chain variable region and the light chain variable region of Antibody 4.

Nucleic acid sequences encoding heavy chain and light chain of Antibodies 5-7 are depicted in Table 1. However, nucleic acids encoding a heavy or a light chain CDR of an antibody according to the disclosure comprising nucleic acid sequences which differ from the nucleic acid sequences depicted in Table 1 but comprising nucleic acid codons encoding the amino acid sequence of the heavy chain, light chain, heavy chain CDR, or light chain CDR sequence depicted in Table 1 are also encompassed by the disclosure.

Provided is therefore an isolated, synthetic or recombinant nucleic acid comprising a nucleic acid sequence encoding an amino acid sequence that is at least 80%, at least 85%, at least 90%, at least 91%, at least 92%, at least 93%, at least 94%, at least 95%, at least 96%, at least 97%, at least 98%, at least 99%, or 100% identical to any of the sequences of SEQ ID NOs: 1, 2, 3, 5, 6 and 7, or any combinations or fragments thereof. Further provided is an isolated, synthetic or recombinant nucleic acid comprising a nucleic acid sequence encoding an amino acid sequence that is at least 80%, at least 85%, at least 90%, at least 91%, at least 92%, at least 93%, at least 94%, at least 95%, at least 96%, at least 97%, at least 98%, at least 99%, or 100% identical to any of the sequences of SEQ ID NOs: 1, 2, 3, 5, 10, and 11, or any combinations or fragments thereof. Further provided is an isolated, synthetic or recombinant nucleic acid comprising a nucleic acid sequence encoding an amino acid sequence that is at least 80%, at least 85%, at least 90%, at least 91%, at least 92%, at least 93%, at least 94%, at least 95%, at least 96%, at least 97%, at least 98%, at least 99%, or 100% identical to any of the sequences of SEQ ID NOs: 3, 5, 6, 7, 13, and 14, or any combinations or fragments thereof. Further provided is an isolated, synthetic or recombinant nucleic acid comprising a nucleic acid sequence encoding an amino acid sequence that is at least 80%, at least 85%, at least 90%, at least 91%, at least 92%, at least 93%, at least 94%, at least 95%, at least 96%, at least 97%, at least 98%, at least 99%, or 100% identical to any of the sequences of SEQ ID NOs: 3, 5, 10, 11, 13, and 14, or any combinations or fragments thereof.

Further provided is an isolated, synthetic or recombinant nucleic acid comprising a nucleic acid sequence encoding an amino acid sequence that is at least 80%, at least 85%, at least 90%, at least 91%, at least 92%, at least 93%, at least 94%, at least 95%, at least 96%, at least 97%, at least 98%, at least 99%, or 100% identical to any of the sequences of SEQ ID NOs: 4 and 8, or any combinations or fragments thereof. Further provided is an isolated, synthetic or recombinant nucleic acid comprising a nucleic acid sequence encoding an amino acid sequence that is at least 80%, at least 85%, at least 90%, at least 91%, at least 92%, at least 93%, at least 94%, at least 95%, at least 96%, at least 97%, at least 98%, at least 99%, or 100% identical to any of the sequences of SEQ ID NOs: 4 and 12, or any combinations or fragments thereof. Further provided is an isolated, synthetic or recombinant nucleic acid comprising a nucleic acid sequence encoding an amino acid sequence that is at least 80%, at least 85%, at least 90%, at least 91%, at least 92%, at least 93%, at least 94%, at least 95%, at least 96%, at least 97%, at least 98%, at least 99%, or 100% identical to any of the sequences of SEQ ID NOs: 8 and 16, or any combinations or fragments thereof. Further provided is an isolated, synthetic or recombinant nucleic acid comprising a nucleic acid sequence encoding an amino acid sequence that is at least 80%, at least 85%, at least 90%, at least 91%, at least 92%, at least 93%, at least 94%, at least 95%, at least 96%, at least 97%, at least 98%, at least 99%, or 100% identical to any of the sequences of SEQ ID NOs: 12 and 16, or any combinations or fragments thereof. Nucleic acid encoding a heavy and/or light chain CDR or an antibody that is modified for instance by conservative amino acid substitution, are also encompassed by the disclosure.

In some embodiments, a nucleic acid or nucleic acid sequence according to the disclosure comprises a chain of nucleotides, (i.e., DNA and/or RNA). However, a nucleic acid or nucleic acid sequence of the disclosure may comprise other kinds of nucleic acid structures such as for instance a DNA/RNA helix, peptide nucleic acid (PNA), locked nucleic acid (LNA) and/or a ribozyme. Such other nucleic acid structures are referred to as functional equivalents of a nucleic acid sequence, and are encompassed by the disclosure. The term "functional equivalent of a nucleic acid sequence" also encompasses a chain comprising non-natural nucleotides, modified nucleotides and/or non-nucleotide building blocks which exhibit the same function as natural nucleotides.

The disclosure further provides a vector comprising one or more nucleic acids according to the disclosure. In some embodiments, the vector is a plasmid. A plasmid is defined herein as a circular. In some embodiments, the plasmid is a double-stranded, DNA molecule. Methods for preparing a vector comprising a nucleic acid according to the disclosure are well known in the art. Non-limiting examples of vectors suitable for generating a vector of the disclosure are retroviral and lentiviral vectors. A vector according to the disclosure can be used for a variety of applications. A vector according to the disclosure is, in some embodiments, used for in vitro expression of a nucleic acid according to the disclosure in a cell, such as for the generation of antibodies or fragments according to the disclosure. Further, a vector according to the disclosure comprising a nucleic acid according to the disclosure can be used for therapeutically. Administration of such vector to an individual, such as a human, in need thereof results in expression of an antibody or fragment according to the disclosure in vivo.

In some embodiments, the disclosure provides for a vector encoding any of the antibodies or fragments disclosed herein. In some embodiments, the vector is a viral vector. In some embodiments, the vector is an AAV vector. Recombinant AAV (rAAV) vectors of the present disclosure may be generated from a variety of adeno-associated viruses. For example, ITRs from any AAV serotype are expected to have similar structures and functions with regard to replication, integration, excision and transcriptional mechanisms. Examples of AAV serotypes include AAV1, AAV2, AAV3, AAV4, AAV5, AAV6, AAV7, AAV8, AAV9, AAV10, AAV11, and AAV12. In some embodiments, the rAAV vector is generated from serotype AAV1, AAV2, AAV4, AAV5, or AAV8. These serotypes are known to target photoreceptor cells or the retinal pigment epithelium. In particular embodiments, the rAAV vector is generated from serotype AAV2. In certain embodiments, the AAV serotypes include AAVrh8, AAVrh8R or AAVrh10. It will also be understood that the rAAV vectors may be chimeras of two or more serotypes selected from serotypes AAV1 through AAV12. The tropism of the vector may be altered by packaging the recombinant genome of one serotype into capsids derived from another AAV serotype. In some embodiments, the ITRs of the rAAV virus may be based on the ITRs of any one of AAV1-12 and may be combined with an AAV capsid selected from any one of AAV1-12, AAV-DJ, AAV-DJ8, AAV-DJ9 or other modified serotypes. In certain embodiments, any AAV capsid serotype may be used with the vectors of the disclosure. Examples of AAV serotypes include AAV1, AAV2, AAV3, AAV4, AAV5, AAV6, AAV7, AAV8, AAV9, AAV10, AAV11, AAV12, AAV-DJ, AAV-DJ8, AAV-DJ9, AAVrh8, AAVrh8R, or AAVrh10. In certain embodiments, the AAV capsid serotype is AAV2.

Further provided is a recombinant cell comprising a nucleic acid or vector according to the disclosure. In some embodiments, the nucleic acid or vector is introduced into the cell so that the cell's nucleic acid translation machinery will produce the encoded antibodies or fragments. In some embodiments, a nucleic acid or vector according to the disclosure is expressed in so called producer cells, such as for instance cells of a Chinese hamster ovary (CHO), NSO (a mouse myeloma) or 293(T) cell line, some of which are adapted to commercial antibody production. Proliferation of such producer cells results in a producer cell line capable of producing antibodies or fragments according to the disclosure. In some embodiments, the producer cell line is suitable for producing antibodies for use in humans. In some embodiments, the producer cell line is free of pathogenic agents such as pathogenic micro-organisms.

The disclosure further provides a method for producing an antibody or fragment according to the disclosure comprising providing a cell with a nucleic acid or a vector according to the disclosure, and allowing the cell to translate the nucleic acid sequence comprised by the nucleic acid or vector, thereby producing the antibody or fragment according to the disclosure. In some embodiments, the method according to the disclosure further comprises harvesting, purifying and/or isolating the antibody or fragment. Antibodies or fragments obtained with a method for producing an antibody or fragment according to the disclosure are also provided.

D. Pharmaceutical Compositions

In some embodiments, the antibody or fragment according to the disclosure can be advantageously used in therapeutic applications. Provided is thus a pharmaceutical composition comprising an antibody or fragment according to the disclosure and a pharmaceutically acceptable carrier, diluent and/or excipient. Also provided are pharmaceutical compositions comprising a nucleic acid or vector (e.g., an AAV vector) according to the disclosure and at least one pharmaceutically acceptable carrier, diluent and/or excipient. Non-limiting examples of suitable carriers are for instance keyhole limpet haemocyanin (KLH), serum albumin (e.g. BSA or RSA) and ovalbumin. In some embodiments, the carrier is a solution, such as an aqueous solution, for example saline, or an oil-based solution. Non-limiting examples of excipients which can be incorporated in tablets, capsules and the like are a binder such as gum tragacanth, acacia, corn starch or gelatin, an excipient such as microcrystalline cellulose, a disintegrating agent such as corn starch, pregelatinized starch and alginic acid, a lubricant such as magnesium stearate, a sweetening agent such as sucrose, lactose or saccharin, and a flavoring agent such as peppermint, oil of wintergreen or cherry. In some embodiments, the dosage unit form is a capsule. In some embodiments, the dosage unit form contains, in addition to one or more of the excipients indicated above, a liquid carrier such as fatty oil. Various other materials may be present as coatings or to modify the physical form of the dosage unit. For instance, tablets may be coated with shellac and/or sugar or both. In some embodiments, a pharmaceutical composition according to the disclosure is suitable for human use.

The pharmaceutical compositions described herein can be administered in a variety of different ways. Examples include administering a pharmaceutical composition comprising an antibody according to the disclosure and containing a pharmaceutically acceptable carrier via intraocular, intravitreal, subretinal, oral, intranasal, rectal, topical, intraperitoneal, intravenous, intramuscular, subcutaneous, subdermal, transdermal, intrathecal, and intracranial methods. In particular embodiments, any of the antibodies, fragments, vectors or pharmaceutical compositions disclosed herein may be administered to a subject intravitreally. In particular embodiments, any of the antibodies, fragments, vectors or pharmaceutical compositions disclosed herein may be administered to a subject subretinally. For oral administration, the active ingredient can be administered in solid dosage forms, such as capsules, tablets, and powders, or in liquid dosage forms, such as elixirs, syrups, and suspensions. Sterile compositions for injection can be formulated according to conventional pharmaceutical practice by dissolving or suspending the antibody or fragment of the disclosure in a vehicle for injection, such as water or a naturally occurring oil like sesame oil, coconut oil, peanut oil, cottonseed oil, etc., or a synthetic fatty vehicle like ethyl oleate. Buffers, preservatives and/or antioxidants may also be incorporated.

E. Therapeutic/Prophylactic Applications

The disclosure further provides an antibody or fragment according to the disclosure for use in therapy. Further provided is a nucleic acid according to the disclosure for use in therapy. The therapy can be therapeutic or prophylactic.

Antibodies or fragments according to the disclosure are particularly suitable for the treatment, alleviation or prevention of a disorder associated with alternative pathway complement activation. Provided is therefore an antibody or fragment according to the disclosure for use in the treatment, alleviation or prevention of a disorder associated with alternative pathway complement activation. Also provided is a nucleic acid according to the disclosure for use in the treatment, alleviation or prevention of a disorder associated with alternative pathway complement activation. As used herein "a disorder associated with alternative complement activation" is herein defined as a disorder wherein unwanted and/or excessive alternative pathway complement activation leads to cell, tissue or extracellular matrix damage. Cells that may be damaged by unwanted and/or excessive alternative pathway activation are any cell that is in contact with blood, for instance red blood cells, epithelial cells, in particular hepatic and/or kidney epithelial cells, platelets, white blood cells, endothelial cells. In some embodiments, the disorder is a disorder associated with impaired FH function or FH deficiency. In some embodiments, the disorder is a disorder associated with impaired FH function or FH deficiency but not with FH absence. Since the antibodies and fragments of the disclosure potentiate the function of FH, the antibodies and fragment are particularly suitable to block or reduce the effects of impaired FH function or FH deficiency. However, the potentiating anti-FH antibodies of the disclosure may also inhibit lysis of red blood cells that are incubated with serum of healthy individuals in which FH is artificially blocked. Hence, antibodies and fragments can also be used to block or reduce unwanted and/or excessive alternative pathway complement activation caused by factors other than impaired FH function or FH deficiency. Non-limiting examples of such orders that can be treated are atypical hemolytic uremic syndrome (aHUS), paroxysmal nocturnal hemoglobinuria (PNH), age-related macular degeneration (AMD), membranoproliferative glomerulonephritis (MPGN).

Atypical hemolytic uremic syndrome (aHUS), also referred to as complement mediated HUS, is characterized by hemolytic anemia, thrombocytopenia, systemic thrombotic microangiopathy (TMA) and renal failure. The onset of aHUS is typically in childhood and episodes of the disease are associated with e.g. infection, pregnancy, other disease, surgery, or trauma. Over 60% of aHUS patients die or develop end stage renal disease (ESRD) despite plasma exchange or plasma supplementation. Several mutations in components or factors of the complement system have been identified in patients with aHUS. Mutations in FH, FI FB, membrane cofactor protein (MCP), thrombomodulin (THBD) or C3 comprise about 50% of the known mutations in patients with aHUS of which mutations of FH are the most frequent (about 20-30% of aHUS patients). The majority of patients are heterozygous for the mutations, which nevertheless results in pathological FH deficiency. In addition, in about 10% of patients aHUS is caused by autoantibodies against FH, also resulting in reduced functional FH. Currently the standard treatment for aHUS is plasma supplementation or plasma exchange therapy. In addition eculizumab is used in the treatment of patients with aHUS. Renal transplantation is associated with a high risk of recurrence which is dependent on the mutation underlying aHUS. Transplantation is contraindicated in children with mutations in FH, FB, FI, C3 or THBD due to the increased risk of recurrence. Antibodies or fragments, such as antibodies or fragments comprising at least the Fab fragment, according to the disclosure are particularly suitable for the treatment, alleviation or prevention of aHUS caused by a mutation in FH or by the presence of anti-FH autoantibodies. The potentiating effect on FH is independent on the CCP domain of FH carrying a mutation. For example, potentiating FH antibodies or fragments thereof are able to inhibit alternative complement activation in aHUS patients carrying a mutation in CCP1, CCP6, CCP7, CCP14, CCP17, CCP18, CCP19 and CCP20 of FH. However, since the antibodies and fragments of the disclosure may also potentiate the activity of FH in the absence of impaired FH function or FH deficiency, any form of complement dependent aHUS can be advantageously treated, alleviated or prevented with the antibodies or fragments of the disclosure.

Paroxysmal nocturnal hemoglobinuria (PNH) is caused by a genetic mutation in the X chromosome of a totipotent hematopoietic stem cell. The mutation leads to a deficiency in phosphatidylinositol glycan class A protein, which is critical for the synthesis of glycosylphosphatidylinositol membrane anchoring proteins (GPI-AP). Inhibitor of the complement system CD55 is an example of such protein, which binds C3b at the host cell surface thereby preventing the formation of C3 convertase. Hence, a deficiency of these proteins results in unwanted or excessive complement activation. One of the main consequences of PNH is that red blood cells undergo lysis as a result of the excessive activity of the complement system. Recently, eculizumab has been approved for the treatment of PNH in several countries. Other therapies include blood transfusion, erythrocyte-stimulating agent therapy, treatment with corticosteroids and anabolic steroids. Since the antibodies and fragments of the disclosure may also potentiate the activity of FH independent from the levels of FH or FH function, thereby inhibiting the activation of the alternative pathway of the complement system, the antibodies and fragment can be advantageously used in PNH patients. In addition, because the antibodies and fragments of the disclosure act at the level of C3 deposition, as opposed to eculizumab that acts more downstream of the activation pathways, depletion of cells in the liver is reduced because less cells are opsonized by C3b.

Age-related macular degeneration (AMD) is damage to the retina affects usually affecting older individuals resulting in a loss of vision in the macula, the center of the visual field. Mutations and SNPs (single nucleotide polymorphisms) in FH have recently been implicated in about 35% of AMD patients. The SNP is located in CCP7 of FH and was demonstrated to influence the binding of FH to heparin thereby compromising the ability of FH to bind the host cell surface as well as the extracellular matrix. Antibodies or fragments, such as antibodies or fragments comprising at least the Fab fragment, according to the disclosure are particularly suitable for the treatment, alleviation or prevention AMD characterized by decreased FH function, (i.e., by a SNP in the gene encoding FH).

Membranoproliferative glomerulonephritis (MPGN) is an uncommon cause of chronic nephritis that occurs primarily in children and young adults. It causes glomerular injury as a result of proliferation of mesangial and endothelial cells and expansion of the mesangial matrix, thickening of the peripheral capillary walls by subendothelial immune deposits and/or intramembranous dense deposits, and mesangial interposition into the capillary wall. MPGN is often associated with a total absence of FH. In some embodiments, MPGN that can be treated with antibodies and/or fragments of the disclosures is associated with impaired FH function or FH deficiency but not with FH absence.

The disclosure thus provides an antibody or fragment or nucleic acid according to the disclosure for use in the treatment, alleviation or prevention of a disorder associated with alternative pathway complement activation. In some embodiments, the disorder is selected from the group consisting of atypical haemolytic uremic syndrome (aHUS), paroxysmal nocturnal hemoglobinuria (PNH), age-related macular degeneration (AMD), membranoproliferative glomerulonephritis (MPGN). Also provided is the use of an antibody or fragment, a nucleic acid or a vector according to the disclosure for the preparation of a medicament for the treatment, alleviation or prevention of a disorder associated with alternative pathway complement activation. In some embodiments, the disorder is selected from the group consisting of atypical haemolytic uremic syndrome (aHUS), paroxysmal nocturnal hemoglobinuria (PNH), age-related macular degeneration (AMD), membranoproliferative glomerulonephritis (MPGN), and IgA Nephropathy. In particular embodiments, the disorder is IgA Nephropathy. In some embodiments, the antibodies or fragments for use as a medicament or prophylactic agent in accordance with the disclosure are antibodies or fragments thereof (i.e., the Fab, Fab' or F(ab)$_2$ or F(ab')2 fragment) that comprise the heavy and light chain CDR1, CDR2 and CDR3 of antibody as depicted in Table 1. In some embodiments, the antibody or fragment is a monoclonal humanized or chimeric antibody or fragment.

The disclosure further provides a method for inhibiting alternative complement activation comprising administering to an individual an antibody or fragment according to the disclosure, or a nucleic acid or a vector according to the disclosure. The disclosure further provides a method for treating, alleviating, or preventing a disorder associated with alternative pathway complement activation comprising administering to an individual in need thereof a therapeutically effective amount of an antibody or fragment according to the disclosure. Also provided is a method for treating, alleviating, or preventing a disorder associated with alternative pathway complement activation comprising administering to an individual in need thereof a therapeutically effective amount of a nucleic acid or vector according the disclosure. Further provided is a method for treating, alleviating, or preventing a disorder associated with alternative pathway complement activation comprising administering to an individual in need thereof a therapeutically effective amount of a pharmaceutical composition according to the disclosure. In some embodiments, the disorder is selected from the group consisting of atypical hemolytic uremic syndrome (aHUS), paroxysmal nocturnal hemoglobinuria (PNH), age-related macular degeneration (AMD), membranoproliferative glomerulonephritis (MPGN). As used herein, an "individual" is a human or an animal that has a complement system as part of its immune system (e.g., a mammal). In a particular embodiment the individual is a human. In some embodiments, the antibodies for use in the methods of the disclosure are antibodies or fragments thereof, such as the Fab, Fab', F(ab)$_2$ or F(ab')2 fragment, that comprise the heavy and light chain CDR1, CDR2 and CDR3 of Antibody 1; the heavy and light chain CDR1, CDR2 and CDR3 of Antibody 2; the heavy and light chain CDR1, CDR2 and CDR3 of Antibody 3; or the heavy and light chain CDR1, CDR2 and CDR3 of Antibody 4. In some embodiments, the antibody or fragment is a monoclonal humanized or chimeric antibody or fragment.

The compositions containing the antibodies, fragments, nucleic acids of the disclosure can be administered for prophylactic and/or therapeutic treatments. In therapeutic applications antibodies, fragment, nucleic acids or compositions according to the disclosure are administered to an individual, (e.g., a human), already suffering from a disease and/or already showing symptoms of the disease in an amount sufficient to counteract the symptoms of the disease and/or its complications. In prophylactic applications, antibodies, fragment, nucleic acids or compositions according to the disclosure are administered to an individual, before the individual shows symptoms of the disorder to prevent the development of these symptoms or its complications. For instance, individuals that carry a genetic mutation that may or will cause a disorder associated with alternative complement activation can be prophylactically treated with antibodies, fragment, nucleic acids or compositions according to the disclosure. The antibodies, fragment, nucleic acid, or vector molecules are typically present in a pharmaceutical composition according to the disclosure in a therapeutically effective amount, which is an amount sufficient to remedy the disorder associated with unwanted or excessive activation of the alternative pathway of the complement system.

Features may be described herein as part of the same or separate aspects or embodiments of the present disclosure for the purpose of clarity and a concise description. It will be appreciated by the skilled person that the scope of the disclosure may include embodiments having combinations of all or some of the features described herein as part of the same or separate embodiments.

Examples

These examples are provided for illustrative purposes only and not to limit the scope of the claims provided herein.
Reagents Human purified factor H was obtained from CompTech. (Tyler, Texas USA). Rat anti-mouse kappa (RM19) was obtained from Sanquin (Business Unit reagents, Sanquin, Amsterdam, the Netherlands). High performance ELISA buffer (HPE) was obtained from Sanquin. Recombinant FH CCPs (CCP 15-18, CCP 15-19, CCP 18-20, or CCP 19-10) was produced as described before (Schmidt et al. 2008). Mouse monoclonal antibodies (mAbs) against human FH were made as previously described. Anti-IL-6.8 was used as isotype control and was obtained from Sanquin. Anti-C3.19 may react with an epitope on the C3d fragment of the molecule (Wolbink et al. 1993).
Expression of rhFHR Proteins Recombinant human factor H-related (rhFHR) proteins, containing a C-terminal 6×-histidine (6×His) tag, were produced and purified as previously described (Pouw et al. 2015). In short, proteins were expressed by transient transfection of pcDNA3.1 expression vectors in HEK293F cells, after which proteins were purified from the supernatant by Ni$^{2+}$ affinity chromatography using HisTrap™ High Performance 1 ml columns (GE Healthcare Life Sciences, Freiburg, Germany). rhFHRs were filtered and concentrated using Amicon® Ultra Centrifugal Filter Devices (Merck Millipore, Darmstadt, Germany).
Antibody Generation Monoclonal antibody FHR-1.3B4 generated by immunizing BALB/c mice intraperitoneally with 25 µg recombinant human factor H-related protein 1 (FHR-1) with 25 rhFHR-1 in montanide as adjuvants at four week intervals. Three days after the fourth booster immunization, spleen cells were fused with the myeloma cell line SP2/0. The presence of FHR-1 specific antibodies in the supernatants of the hybridomas was tested by ELISA. Briefly, microtiter plates were coated with a rat anti-mouse kappa moAb (RM19) to capture mouse IgG antibodies. Specificity of the antibodies was determined by biotinylated rhFHR-1. Briefly, binding of biotinylated rhFHR-1 was determined by incubation with 0.1% (v/v) streptavidin conjugated with HRP, in HPE for 30 min. The ELISA was further developed using 100 μg/mL 3,5,3',5'-tetramethylbenzidine (TMB) in 0.1 M sodium acetate containing 0.003% (v/v) $H_2O_2$, pH 5.5. Substrate conversion was stopped by addition of 100 μL $H_2SO_4$ and absorbance was measured at 450 nm and corrected for the absorbance at 540 nm with a Synergy 2 Multi-Mode plate reader (BioTek Instruments, Winooski, VT, USA). All ELISA steps were performed with a final volume of 100 μL per well.

The FHR-1.3B4 antibody was humanized by grafting the CDR sequences into the framework regions of a human germline antibody. Antibody 5 was produced as a result of humanization. Certain amino acids were then mutated in Antibody 5 to improve the binding affinity to FH. Antibody 1, Antibody 2, Antibody 3, and Antibody 4, as disclosed in Table 1, were the antibodies that exhibited the highest affinities to FH.

Binding Affinity of Antibody to Factor H

To determine binding affinity of Antibodies 1-4, surface plasmon resonance (SPR) experiments were performed using a BiaCore T200 (GE Healthcare) and CM5 sensor chips (GE Healthcare) in accordance with the manufacturer's instructions. Briefly, Antibodies 1-9 or anti-FHR-1.3B4 were captured onto a Protein A or Protein G coupled chip and full length FH was flown over the captured moAB at decreasing concentrations. Binding kinetics obtained from SPR experiment are presented in Table 2.

TABLE 2

Binding kinetics for Antibodies 1-9.

| SampleID (concentration = 200 nM) | $k_{on}$ ± SEM (number of replicates used), $M^{-1} s^{-1}$ | $K_{off}$ ± SEM (number of replicates used), $s^{-1}$ | Kd ± SEM (number of replicates used), nM |
|---|---|---|---|
| FHR-1.3B4 | 59454 ± 2807 (11) | 5.32E−05 ± 2.4E−06 (12) | 0.91 ± 0.05 (11) |
| Antibody 5 | 56674 ± 2131 (11) | 6.16E−04 ± 9.5E−06 (12) | 11.00 ± 0.48 (11) |
| Antibody 6 | 47853 ± 2196 (12) | 2.57E−04 ± 5.2E−06 (12) | 5.45 ± 0.16 (12) |
| Antibody 7 | 48672 ± 1459 (12) | 3.04E−04 ± 5.2E−06 (12) | 6.28 ± 0.14 (12) |
| Antibody 8 | 54558 ± 1570 (12) | 4.81E−05 ± 2.6E−06 (11) | 0.90 ± 0.06 (11) |
| Antibody 9 | 59697 ± 1441 (12) | 5.79E−05 ± 2.6E−06 (11) | 0.98 ± 0.06 (11) |
| Antibody 1 | 53844 ± 1784 (6) | 2.67E−05 ± 2.5E−06 (6) | 0.50 ± 0.05 (6) |
| Antibody 2 | 58499 ± 3557 (6) | 3.06E−05 ± 3.7E−06 (6) | 0.52 ± 0.04 (6) |
| Antibody 3 | 48544 ± 2050 (6) | 4.07E−05 ± 4.0E−06 (4) | 0.85 ± 0.06 (4) |
| Antibody 4 | 55264 ± 1692 (6) | 3.14E−05 ± 4.9E−06 (6) | 0.58 ± 0.10 (6) |

As shown in Table 2, Antibody 1, Antibody 2, Antibody 3, and Antibody 4, bound human FH with nanomolar or sub-nanomolar affinities. Additionally, Antibodies 1-4 had higher binding affinities than that of FHR-1.3B4 for full length FH.

Epitope Mapping mAbs and Competition Assay

Binding site of certain monoclonal antibodies (mAbs) was mapped. Specifically, the reactivity of the mAbs was tested against recombinant FH fragments comprising varying CCP domains (CCP 15-18, CCP 15-19, CCP 18-20, and CCP 19-20) and full length human FH. Location of the epitope of mAbs, such as those disclosed in Table 1, was determined using recombinant human FH fragments composed of multiple CCP domains (15-18, 15-19, 18-20 or 19-20). Briefly, FH.07 and FHR-1.3B4 were captured on a RM-19 coated microtiter plate to assure optimal binding conformation. Next, biotinylated FH, mixed with a 100-fold higher concentration of the indicated unlabeled recombinant FH-fragments, was incubated on the plate for 1 hour. Binding of biotinylated FH was determined by incubation with 0.01% (v/v) streptavidin conjugated with poly-HRP, in HPE for 30 min. The ELISA was further developed as described previously. FH.07 and FHR-1.3B4 were found to bind CCP 18 of human FH.

Competition assays using antibodies or fragments disclosed in Table 1 were performed with agonistic anti-FH antibody FH.07. To determine whether the humanized anti-FHR-1 mAbs disclosed in Table 1 would compete with FH.07 for the binding of FH, a similar set-up as described above was used. Briefly, mAbs were directly coated to the plate and binding of biotinylated FH (FH-bt) in the absence or presence of a 10-fold higher concentration of indicated mAbs was assessed by ELISA as described previously. FHR-1.3B4 was found to compete with FH.07.

C3 Deposition on LPS

To investigate whether Antibodies 1-4 have an effect on alternative pathway inhibition by FH, a C3 deposition assay on LPS was performed. Briefly, 96-wells microtiter plates (Nunc) were coated with Salmonella typhosa LPS (40 μg/mL, L-6386 Sigma-Aldrich) in PBS, overnight at room temperature. LPS was used to activate the alternative pathway of complement. The plates were washed with PBS+ 0.1% (w/v) Tween-20, 10% (v/v). Normal human serum (NHS, final concentration of 10% (v/v)) incubated in Veronal buffer (VB; 3 mM barbital, 1.8 mM sodium barbital, 145 mM NaCl, pH 7.4) containing 0.05% (w/v) gelatin, 5 mM $MgCl_2$, 10 mM EGTA and 0.1% (w/v) Tween-20 in the presence or absence of anti-FH/anti-FHR-1 mAbs (Antibodies 1-4 or FHR-1.3B4), isotype controls or aIL6-8 AB as a negative control at indicated concentrations. C3b deposition was detected with biotinylated mAb anti-C3.19 (0.55 μg/mL in HPE) followed by incubation with 0.01% (v/v) streptavidin conjugated with poly-HRP, in HPE for 30 min. The ELISA was developed as described above. Table 3 describes the $IC_{50}$ values for Antibodies 1-4 and FHR-1.3B4. Table 4 describes the $IC_{50}$ values (2 replicates) for Antibodies 1-4.

TABLE 3

$IC_{50}$ values for Antibodies 1-4 and FHR-1.3B4.

| Antibody | μg/ml | nM |
|---|---|---|
| 1 | 2.26 | 15.07 |
| 2 | 2.82 | 18.79 |
| 3 | 3.47 | 23.12 |
| 4 | 3.51 | 23.4 |
| FHR-1.3B4 | 5.7 | 38.01 |

TABLE 4

$IC_{50}$ values for Antibodies 1-4.

| | Replicate 1 | | Replicate 2 | |
|---|---|---|---|---|
| Antibody | μg/ml | nM | μg/ml | nM |
| 1 | 3.5 | 23.35 | 2.26 | 15.07 |
| 2 | 3.68 | 24.53 | 2.82 | 18.79 |

TABLE 4-continued

IC$_{50}$ values for Antibodies 1-4.

| Antibody | Replicate 1 | | Replicate 2 | |
|---|---|---|---|---|
| | μg/ml | nM | μg/ml | nM |
| 3 | 4.14 | 27.59 | 3.47 | 23.12 |
| 4 | 4.34 | 28.95 | 3.51 | 23.4 |

As shown in Tables 3 and 4, Antibodies 1-4 inhibited C3b deposition on LPS. This indicated that the inhibitory function of FH on alternative pathway activation was strengthened by the addition of Antibody 1, 2, 3, or 4. Additionally, as shown in Table 3, Antibodies 1-4 were more effective in inhibiting C3b deposition on LPS than FHR-1.3B4 as indicated by lower IC$_{50}$ values.

SRBC Hemolytic Assay

To investigate the effect of Antibodies 1-4 on the function of Factor H, a hemolytic assay generally as described previously by Sanchez-Corral et al. (2004) and Wouters et al. (2008). Briefly, pre-diluted human serum (20%, v/v), containing 20 μg/ml anti-FH.09 (a blocking antibody against FH), was pre-incubated with the indicated mAbs (Antibodies 1-4 or FHR-1.3B4) and mixed in a 1-to-1 ratio with sheep red blood cells (SRBCs) to reach a final concentration of 10% (v/v) serum and $1.05 \times 10^8$ cells/ml in VB with 5 mM MgCl$_2$ and 10 mM EGTA, or VB with 10 mM EDTA as blank, followed by incubation at 37° C. for 75 minutes while shaking. Lysis was stopped by adding 100 μl ice-cold VB with 20 mM EDTA followed by centrifugation (2.5 minutes, 1,800 RPM/471 RCF, 7° C.). Hemolysis was measured as absorbance of the supernatants at 412 nm, corrected for background absorbance measured at 690 nm, and expressed as percentage of the 100% lysis control (SRBCs incubated with 0.6% (w/v) Saponin). As negative control, SRBCs were incubated with serum diluted in VB supplemented with 10 mM EDTA to prevent complement activation.

Graphpad prism 7.04 was used to calculate the IC$_{50}$ of hemolysis from multiple experiments using various antibodies, such as those disclosed in Table 1, and statistical comparisons were made by ordinary one-way ANOVA and Dunnett's multiple comparisons test. Table 5 describes the IC$_{50}$ values for antibodies 1-4 and FHR-1.3B4. Table 6 describes the IC$_{50}$ values (2 replicates) for antibodies 1-4.

TABLE 5

IC$_{50}$ values for antibodies 1-4 and FHR-1.3B4.

| Antibody | ug/ml | nM |
|---|---|---|
| 1 | 10.6 | 70.7 |
| 2 | 10.1 | 67.3 |
| 3 | 9.4 | 62.7 |
| 4 | 11.5 | 76.7 |
| FHR-1.3B4 | 11.4 | 76 |

TABLE 6

IC$_{50}$ values for antibodies 1-4.

| Antibody | μg/ml | nM | μg/ml | nM |
|---|---|---|---|---|
| 1 | 10.7 | 71.33 | 10.9 | 72.67 |
| 2 | 11.45 | 76.33 | 10.4 | 69.33 |

TABLE 6-continued

IC$_{50}$ values for antibodies 1-4.

| Antibody | μg/ml | nM | μg/ml | nM |
|---|---|---|---|---|
| 3 | 11.1 | 74 | 9.1 | 60.67 |
| 4 | 11.47 | 76.47 | 11.78 | 78.53 |

As shown in Tables 5 and 6, Antibodies 1-4 inhibited SRBC lysis. Additionally, as shown in Table 6, Antibodies 1-3 were more effective in inhibiting SRBC lysis than FHR-1.3B4 as indicated by lower IC$_{50}$ values.

Binding Affinity of Factor H to C3b in the Presence of Anti-FH Antibodies

Binding of FH to C3b in the presence of Antibodies 1-4, such as those disclosed in Table 1, was determined by surface plasmon resonance using a Biacore T200 instrument (GE Healthcare, Little Chalfont, UK). Specifically, purified C3b (Complement Technologies) were immobilized onto a flow cell of a CM5 Biacore Sensor Chip (GE Healthcare) using standard amine coupling. The remaining flow cell was used as reference surface and prepared by performing a coupling reaction without the addition of any protein. A response of 2000 response units (RUs) was obtained after coupling with C3b. SPR experiments was performed at 37° C. using a flow rate of 10 μl/min and in phosphate buffered saline pH 7.4 (PBS, Orphi Farma) supplemented with 0.01% (w/v) Tween-20 (Merck) (PBS-T).

To determine the effect of the antibodies without interference of possible cross-linking via the moAb, recombinantly produced Fab' fragments of the mAbs (Antibodies 1-4) were used. Fab' fragments were mixed with plasma purified FH (pdFH). FH was injected for 60 seconds at different concentrations (10-0.01953 μM for FH alone and 5-0.01953 μM for complexed with moAb Fab' fragments) over the chip in absence or presence of 10 μM (at least 2 fold molar ratio excess) of anti-FHR-1 3B4 Fab' fragments or Fab' fragments of Antibodies 1-4. Each Fab' fragment was also injected without addition of FH to determine any interactions of the Fab' fragments with the surfaces. The pdFH injection was followed by a dissociation of 60 seconds and surface was regenerated between each cycle by a single injection of 1 M NaCl (Merck).

Data was analyzed using Scrubber 2 (Biologic Software) and affinities were determined by equilibrium analysis. Table 7 lists the binding kinetics for Antibodies 1-4.

TABLE 7

Binding kinetics for Antibodies 1-4 (Fab' fragments).

| Name | K$_D$ (number of replicates used) |
|---|---|
| pdFH | 1.3 μM (2) |
| pdFH + FHR-1.3B4 (Fab' fragment) | 299 nM (9) |
| pdFH + Antibody 1 (Fab' fragment) | 273 nM (7) |
| pdFH + Antibody 2 (Fab' fragment) | 284 nM (7) |
| pdFH + Antibody 3 (Fab' fragment) | 336 nM (9) |
| pdFH + Antibody 4 (Fab' fragment) | 292 nM (8) |

As shown in Table 7, the addition of Fab' fragments of Antibodies 1-4 increased the response on the C3b coated surface, indicating that Antibodies 1-4 enhanced the binding of pdFH to C3b.

REFERENCES

Almagro J C, Fransson J. 2008. Humanization of antibodies. Frontiers in Bioscience 13: 1619-33.

Carter P, Presta L, Gorman C M, Ridgway J B, Henner D, Wong W L, Rowland A M, Kotts C, Carver M E, Shepard H M. 1992. Humanization of an anti-p185HER2 antibody for human cancer therapy. Proc. Natl. Acad. Sci. U.S.A. 89(10):4285-9.

Chen Y, Wiesmann C, Fuh G, Li B, Christinger H W, McKay P, de Vos A M, Lowman H B. Selection and analysis of an optimized anti-VEGF antibody: crystal structure of an affinity-matured Fab in complex with antigen. J Mol Biol. 1999; 293(4):865-81.

Cheng Z Z, Corey M J, Parepalo M, Majno S, Hellwage J, Zipfel P F, Kinders R J, Raitanen M, Meri S, Jokiranta T S. Complement factor H as a marker for detection of bladder cancer. Clin Chem. 2005; 51(5): 856-63.

Corey M J, Kinders R J, Poduje C M, Bruce C L, Rowley H, Brown L G, Hass G M, Vessella R L. Mechanistic studies of the effects of anti-factor H antibodies on complement-mediated lysis. J Biol Chem. 2000; 275 (17):12917-25.

Lazar G A1, Desjarlais J R, Jacinto J, Karki S, Hammond P W. 2007. A molecular immunology approach to antibody humanization and functional optimization. Mol. Immunol., 44(8):1986-98.

Lefranc M P, "Unique database numbering system for immunogenetic analysis" Immunology Today, 18, 509 (1997). PMID: 9386342.

Lefranc M P, "The IMGT unique numbering for immunoglobulins, T cell Receptors and Ig-like domains", The Immunologist. 1999; 7, 132-136.

Lefranc M P, Pommié C, Ruiz M, Giudicelli V, Foulquier E, Truong L, Thouvenin-Contet V, and Lefranc G, "IMGT unique numbering for immunoglobulin and T cell receptor variable domains and Ig superfamily V-like domains" Dev. Comp. Immunol., 27, 55-77 (2003). PMID 12477501.

Padlan, E A. 1991. A possible procedure for reducing the immunogenicity of antibody variable domains while preserving their ligand-binding properties. Mol. Immunol., 28(4-5):489-98.

Pouw, Richard B, Mieke C Brouwer, Judy Geissler, Laurens V van Herpen, Sacha S Zeerleder, Walter A Wuillemin, Diana Wouters, and Taco W Kuijpers. 2016. "Complement Factor H-Related Protein 3 Serum Levels Are Low Compared to Factor H and Mainly Determined by Gene Copy Number Variation in CFHR3." PLoS ONE 11 (3): e0152164.

Queen C, Schneider W P, Selick H E, Payne P W, Landolfi N F, Duncan J F, Avdalovic N M, Levitt M, Junghans R P, Waldmann T A. 1989. A humanized antibody that binds to the interleukin 2 receptor. Proc. Natl. Acad. Sci. U.S.A. 86(24):10029-33.

Sánchez-Corral, Pilar, C Gonzalez-Rubio, Santiago Rodriguez de Córdoba, and Margarita López-Trascasa. 2004. "Functional Analysis in Serum from Atypical Hemolytic Uremic Syndrome Patients Reveals Impaired Protection of Host Cells Associated with Mutations in Factor H." Molecular Immunology 41 (1): 81-84.

Schmidt, Christoph Q, Andrew P Herbert, Henry G Hocking, D Uhrín, and Paul N Barlow. 2008. "Translational Mini-Review Series on Complement Factor H: Structural and Functional Correlations for Factor H." Clinical and Experimental Immunology 151 (1): 14-24.

Tan P, Mitchell D A, Buss T N, Holmes M A, Anasetti C, Foote J. 2002. "Superhumanized" antibodies: reduction of immunogenic potential by complementarity-determining region grafting with human germline sequences: application to an anti-CD28. J. Immunol., 169(2):1119-25.

Wolbink, G J, J Bollen, J W Baars, R J ten Berge, a J Swaak, J Paardekooper, and C Erik Hack. 1993. "Application of a Monoclonal Antibody against a Neoepitope on Activated C4 in an ELISA for the Quantification of Complement Activation via the Classical Pathway." Journal of Immunological Methods 163 (1): 67-76.

Wouters, Diana, Mieke C Brouwer, Mohamed R Daha, and C Erik Hack. 2008. "Studies on the Haemolytic Activity of Circulating C1q-C3/C4 Complexes." Molecular Immunology 45 (7): 1893-99.

INCORPORATION BY REFERENCE

All publications, patents, and patent applications mentioned in this specification are herein incorporated by reference to the same extent as if each individual publication, patent, or patent application was specifically and individually indicated to be incorporated by reference.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. An isolated, synthetic or recombinant antibody or an antigen binding fragment thereof that specifically binds to complement control protein domain 18 (CCP18) of factor H (FH) comprising:
   a light chain CDR1 sequence comprising the sequence SSVTY (SEQ ID NO: 1) or the sequence TSVTY (SEQ ID NO: 13),
   a light chain CDR2 sequence comprising the sequence ATS (SEQ ID NO: 2) or the sequence AS(SEQ ID NO: 14),
   a light chain CDR3 sequence comprising the sequence QHRSSSNPLT (SEQ ID NO: 3),
   a heavy chain CDR1 sequence comprising the sequence GFSLTNYG (SEQ ID NO: 5),
   a heavy chain CDR2 sequence comprising the sequence VWSGGTT (SEQ ID NO: 6) or the sequence of IWSGGTT (SEQ ID NO: 10), and
   a heavy chain CDR3 sequence comprising the sequence ARNFGNYAMDY (SEQ ID NO: 7) or the sequence ARNFGNYAMDF (SEQ ID NO: 11).

2. The antibody or fragment according to claim 1, comprising:
   a light chain CDR1 sequence comprising the sequence SSVTY (SEQ ID NO: 1),
   a light chain CDR2 sequence comprising the sequence ATS (SEQ ID NO: 2),
   a light chain CDR3 sequence comprising the sequence QHRSSSNPLT (SEQ ID NO: 3),
   a heavy chain CDR1 sequence comprising the sequence GFSLTNYG (SEQ ID NO: 5),
   a heavy chain CDR2 sequence comprising the sequence IWSGGTT (SEQ ID NO: 10), and
   a heavy chain CDR3 sequence comprising the sequence ARNFGNYAMDF (SEQ ID NO: 11).

3. The antibody or fragment according to claim 1, comprising:
   a light chain CDR1 sequence comprising the sequence SSVTY (SEQ ID NO: 1),
   a light chain CDR2 sequence comprising the sequence ATS (SEQ ID NO: 2),
   a light chain CDR3 sequence comprising the sequence QHRSSSNPLT (SEQ ID NO: 3),
   a heavy chain CDR1 sequence comprising the sequence GFSLTNYG (SEQ ID NO: 5),
   a heavy chain CDR2 sequence comprising the sequence VWSGGTT (SEQ ID NO: 6), and
   a heavy chain CDR3 sequence comprising the sequence ARNFGNYAMDY (SEQ ID NO: 7).

4. The antibody or fragment according to claim 1, comprising:
   a light chain CDR1 sequence comprising the sequence TSVTY (SEQ ID NO: 13),
   a light chain CDR2 sequence comprising the sequence AS(SEQ ID NO: 14),
   a light chain CDR3 sequence comprising the sequence QHRSSSNPLT (SEQ ID NO: 3),
   a heavy chain CDR1 sequence comprising the sequence GFSLTNYG (SEQ ID NO: 5),
   a heavy chain CDR2 sequence comprising the sequence VWSGGTT (SEQ ID NO: 6), and
   a heavy chain CDR3 sequence having the sequence ARNFGNYAMDY (SEQ ID NO: 7).

5. The antibody or fragment according to claim 1, comprising:
   a light chain CDR1 sequence comprising the sequence TSVTY (SEQ ID NO: 13),
   a light chain CDR2 sequence comprising the sequence ASS (SEQ ID NO: 14),
   a light chain CDR3 sequence comprising the sequence QHRSSSNPLT (SEQ ID NO: 3),
   a heavy chain CDR1 sequence comprising the sequence GFSLTNYG (SEQ ID NO: 5),
   a heavy chain CDR2 sequence comprising the sequence IWSGGTT (SEQ ID NO: 10), and
   a heavy chain CDR3 sequence comprising the sequence ARNFGNYAMDF (SEQ ID NO: 11).

6. The antibody or fragment according to claim 1, wherein the antibody or fragment has a binding affinity for FH with a $K_D$ of $2.5 \times 10^{-8}$ M or less and/or a binding affinity for a FH fragment comprised of CCP18-20 with a $K_D$ of $0.1 \times 10^{-9}$ M or less.

7. The antibody or fragment according to claim 1, wherein the antibody or fragment has a binding affinity for FH with a $K_D$ of $0.6 \times 10^{-8}$ M or less and/or a binding affinity for a FH fragment comprised of CCP18-20 with a $K_D$ of $0.6 \times 10^{-11}$ M or less.

8. The antibody or fragment according to claim 1, wherein the antibody or fragment:
   inhibits C3b deposition on lipopolysaccharide in vitro with an $IC_{50}$ value of 38 nM or less, in the presence of 10% (v/v) serum;
   inhibits hemolytic activity in vitro with an $IC_{50}$ value of 150 nM or less, in the presence of 10% (v/v) serum;
   decreases $K_D$ (increases binding affinity) of FH for C3b in vitro to at most 2 µM; and/or
   increases binding affinity of FH for C3b in vitro by at least 3-fold.

9. The antibody or fragment according to claim 1, comprising:
   a variable light chain sequence comprising a sequence which has at least 95% sequence identity to SEQ ID NO: 4 or SEQ ID NO: 16; and
   a variable heavy chain sequence comprising a sequence which has at least 95% sequence identity to SEQ ID NO: 8 or SEQ ID NO: 12.

10. The antibody or fragment according to claim 3, comprising a variable light chain sequence comprising SEQ ID NO: 4 and a variable heavy chain sequence comprising SEQ ID NO: 8.

11. The antibody or fragment according to claim 2, comprising a variable light chain sequence comprising SEQ ID NO: 4 and a variable heavy chain sequence comprising SEQ ID NO: 12.

12. The antibody or fragment according to claim 4, comprising a variable light chain sequence comprising SEQ ID NO: 16 and a variable heavy chain sequence comprising SEQ ID NO: 8.

13. The antibody or fragment according to claim 5, comprising a variable light chain sequence comprising SEQ ID NO: 16 and a variable heavy chain sequence comprising SEQ ID NO: 12.

14. The antibody or fragment according to claim 1, wherein the antibody or fragment potentiates an FH activity, wherein the FH activity is inhibition of alternative complement activation represented by:
   an inhibition of hemolytic activity,
   an inhibition of complement component 3 (C3b) deposition, and/or
   an increase of binding of FH to C3b, iC3b, and/or C3d.

15. The antibody or fragment according to claim 1, wherein the antibody or fragment comprises an immunoglobulin heavy chain variable region and an immunoglobulin light chain variable region, and further comprises an immunoglobulin heavy chain constant region and an immunoglobulin light chain constant region.

16. The antibody or fragment according to claim 1, wherein the antibody or fragment comprises a Fab fragment.

17. The antibody or fragment according to claim 1, wherein the antibody or fragment is monoclonal.

18. The antibody or fragment according to claim 1, wherein the antibody or fragment comprises human light chain and heavy chain constant regions.

19. The antibody or fragment according to claim 1, wherein the antibody or fragment is PEGylated.

20. The antibody or fragment according to claim 19, wherein the antibody or fragment is a PEGylated Fab fragment.

21. The antibody or fragment according to claim 18, wherein the constant regions comprise the Fc domain of human IgG4.

22. The antibody or fragment according to claim 21, wherein the Fc domain of human IgG4 comprises amino acid residue Ala or Gln at position 297.

* * * * *

SEQUENCE LISTING

```
<160> NUMBER OF SEQ ID NOS: 52

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1
```

Ser Ser Val Thr Tyr
1               5

<210> SEQ ID NO 2
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Thr Ser
1

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln His Arg Ser Ser Ser Asn Pro Leu Thr
1               5                   10

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Gln Leu Thr Gln Ser Pro Ser Ser Leu Ser Ala Ser Val Gly
1               5                   10                  15

Asp Arg Val Thr Ile Thr Cys Lys Ala Ser Ser Ser Val Thr Tyr Leu
            20                  25                  30

His Trp Tyr Gln Gln Lys Pro Gly Lys Ala Pro Lys Pro Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln His Arg Ser Ser Ser Asn Pro Leu
                85                  90                  95

Thr Phe Gly Ala Gly Thr Lys Leu Glu Leu Lys
            100                 105

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Phe Ser Leu Thr Asn Tyr Gly
1               5

```
<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Trp Ser Gly Gly Thr Thr
1               5

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Arg Asn Phe Gly Asn Tyr Ala Met Asp Tyr
1               5                   10

<210> SEQ ID NO 8
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val Tyr Trp Ile Arg Gln His Pro Gly Lys Gly Leu Glu Trp Ile
        35                  40                  45

Gly Val Val Trp Ser Gly Gly Thr Thr Glu Phe Asn Pro Ser Leu Lys
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Phe Gly Asn Tyr Ala Met Asp Tyr Trp Gly Gln Gly Thr Ser
            100                 105                 110

Val Thr Val Ser Ser
        115

<210> SEQ ID NO 9

<400> SEQUENCE: 9

000

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10
```

```
Ile Trp Ser Gly Gly Thr Thr
1               5

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Arg Asn Phe Gly Asn Tyr Ala Met Asp Phe
1               5                   10

<210> SEQ ID NO 12
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val Tyr Trp Ile Arg Gln His Pro Gly Lys Gly Leu Glu Trp Ile
        35                  40                  45

Gly Val Ile Trp Ser Gly Gly Thr Thr Glu Tyr Asn Pro Ser Met Lys
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Phe Gly Asn Tyr Ala Met Asp Phe Trp Gly Gln Gly Thr Ser
            100                 105                 110

Val Thr Val Ser Ser
        115

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Thr Ser Val Thr Tyr
1               5

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ser Ser
```

<210> SEQ ID NO 15

<400> SEQUENCE: 15

000

<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Gln Leu Thr Gln Ser Pro Ser Ser Leu Ser Ala Ser Val Gly
1               5                   10                  15

Asp Arg Val Thr Ile Thr Cys Arg Ala Ser Thr Ser Val Thr Tyr Met
            20                  25                  30

His Trp Tyr Gln Gln Lys Pro Gly Lys Ala Pro Lys Pro Leu Ile Tyr
        35                  40                  45

Ala Ser Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln His Arg Ser Ser Ser Asn Pro Leu
                85                  90                  95

Thr Phe Gly Ala Gly Thr Lys Leu Glu Leu Lys
            100                 105

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tcaagtgtca aatac                                                    15

<210> SEQ ID NO 18
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18 gccacatcc                                                            9

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cagcagtgga gtattatccc acccacg                                       27

<210> SEQ ID NO 20
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
caaattgttc tctcccagtc tccaacattc ctgtctgcat ctccaggtga aaggtcaca      60 gtgacttgca gggccagttc aagtgtcaaa tacatgcact ggtatcagca gaaaccagga    120
gcctccccca aaccctggat ttttgccaca tccaacctgg cttctggagt ccctgctcgc    180
ttcagtggca gtgggtctgg gacctcttat tctctcacaa tcagcagagt ggaggctgaa    240
gatgctgcca cttattactg ccagcagtgg agtattatcc acccacgtt cggtaatggg     300 accaagctgg agctgaaac                                                  319

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gatttctcat tagctaggta tggt                                             24

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
atatggagtg gtggaaccgc a                                                21

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gccagaaatt ttggtaacta cgctgtggac tac                                   33

<210> SEQ ID NO 24
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
caggtgcagc tgcagcagtc aggacctggc ctagtgcagc cctctcagag cctgtccatt      60
acctgcacag tctctgattt ctcattagct aggtatggtg tacactggat tcgccagtct    120
ccaggaaagg gtctggagtg gctgggagtg atatggagtg gtggaaccgc agactataat    180

```
gcagctttca tatccagact gaacatcaac aaggacaatt ccaagagcca agttttcttt    240
aaaatgaaca gtctccaagc taatgacaca gccatatatt actgtgccag aaattttggt    300
aactacgctg tggactactg gggtcaagga acctcag                             337
```

```
<210> SEQ ID NO 25
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
```

```
caaattgttc tctcccagtc tccaacaatc ctgtctgcat ctccagggga gaaggtcaca    60
atgacttgca gggccagctc aagtgtaact tacatgcact ggtaccagca gaagccagga    120
tcctccccca aaccctggat ttatgccaca tccaacctgg cttctggagt ccctgctcgc    180
ttcagtggca gtgggtctgg gacctcttac tctctcacaa tcagcagagt ggaggctgaa    240
gatgctgcca cttattactg ccagcagcgc agtagtagta acccgctcac gttcggtgct    300
gggaccaagc tggagctgaa at                                             322
```

```
<210> SEQ ID NO 26
<211> LENGTH: 349
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
```

```
caggtgcagc tgaggcagtc aggacctggc ctagtgcagc cctcacagag cctgtccatc    60
acctgcacag tctctggttt ctcattaact aactatggtg tatattgggt tcgccagtct    120
ccaggaaagg gtctggagtg gctgggagtg atatggagtg aggaaccac tgactatagt     180 gcagctttca tatccagact gagcatcagc aaggacaact ccaagagcca agttttcttt    240
aaaatgaaca gtctgcaagc tgatgacaca gccatatact actgtgccag aatttggcac    300
tacgctatgg actacatggg gtcaaggaac ctcacaccgg tctccacag                349
```

```
<210> SEQ ID NO 27

<400> SEQUENCE: 27

000
```

```
<210> SEQ ID NO 28

<400> SEQUENCE: 28

000
```

```
<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Ser Val Lys Tyr
```

<210> SEQ ID NO 30
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Thr Ser
1

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Gln Trp Ser Ile Ile Pro Pro Thr
1               5

<210> SEQ ID NO 32
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Ile Val Leu Ser Gln Ser Pro Thr Phe Leu Ser Ala Ser Pro Gly
1               5                   10                  15

Glu Lys Val Thr Val Thr Cys Arg Ala Ser Ser Ser Val Lys Tyr Met
                20                  25                  30

His Trp Tyr Gln Gln Lys Pro Gly Ala Ser Pro Lys Pro Trp Ile Phe
            35                  40                  45

Ala Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ile Ile Pro Pro Thr
                85                  90                  95

Phe Gly Asn Gly Thr Lys Leu Glu Leu Lys
            100                 105

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Phe Ser Leu Ala Arg Tyr Gly
1               5

<210> SEQ ID NO 34
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ile Trp Ser Gly Gly Thr Ala
1               5

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Arg Asn Phe Gly Asn Tyr Ala Val Asp Tyr
1               5                   10

<210> SEQ ID NO 36
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Gln Gln Ser Gly Pro Gly Leu Val Gln Pro Ser Gln
1               5                   10                  15

Ser Leu Ser Ile Thr Cys Thr Val Ser Asp Phe Ser Leu Ala Arg Tyr
            20                  25                  30

Gly Val His Trp Ile Arg Gln Ser Pro Gly Lys Gly Leu Glu Trp Leu
        35                  40                  45

Gly Val Ile Trp Ser Gly Gly Thr Ala Asp Tyr Asn Ala Ala Phe Ile
    50                  55                  60

Ser Arg Leu Asn Ile Asn Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95

Arg Asn Phe Gly Asn Tyr Ala Val Asp Tyr Trp Gly Gln Gly Thr Ser
            100                 105                 110

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000
```

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Ser Val Thr Tyr
1               5

<210> SEQ ID NO 46
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Thr Ser
1

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Gln Arg Ser Ser Ser Asn Pro Leu Thr
1               5                   10

<210> SEQ ID NO 48
<211> LENGTH: 107

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Ile Val Leu Ser Gln Ser Pro Thr Ile Leu Ser Ala Ser Pro Gly
1               5                   10                  15

Glu Lys Val Thr Met Thr Cys Arg Ala Ser Ser Ser Val Thr Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Arg Ser Ser Ser Asn Pro Leu
                85                  90                  95

Thr Phe Gly Ala Gly Thr Lys Leu Glu Leu Lys
            100                 105

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Phe Ser Leu Thr Asn Tyr Gly
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ile Trp Ser Gly Gly Thr Thr
1               5

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ala Arg Asn Phe Gly Asn Tyr Ala Met Asp Tyr
1               5                   10

<210> SEQ ID NO 52
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 52

```
Gln Val Gln Leu Arg Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val Tyr Trp Val Arg Gln Ser Pro Gly Lys Gly Leu Glu Trp Leu
        35                  40                  45

Gly Val Ile Trp Ser Gly Gly Thr Thr Asp Tyr Ser Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Asn Phe Gly Asn Tyr Ala Met Asp Tyr Trp Gly Gln Gly Thr Ser
            100                 105                 110

Val Thr Val Ser Ser
            115
```